(12) United States Patent
Chen et al.

(10) Patent No.: US 12,187,811 B2
(45) Date of Patent: Jan. 7, 2025

(54) CYCLIC PEPTIDE COMPOUND SIMULATING NATURAL PRODUCT STRUCTURE, AND METHOD FOR PREPARATION THEREOF

(71) Applicant: Nankai University, Tianjin (CN)

(72) Inventors: Gong Chen, Tianjin (CN); Bo Li, Tianjin (CN); Xinghua Li, Tianjin (CN); Boyang Han, Tianjin (CN); Gang He, Tianjin (CN)

(73) Assignee: Nankai University, Tianjin (CN)

( * ) Notice: Subject to any disclaimer, the term of this patent is extended or adjusted under 35 U.S.C. 154(b) by 197 days.

(21) Appl. No.: 17/610,783

(22) PCT Filed: Jun. 21, 2019

(86) PCT No.: PCT/CN2019/092373
§ 371 (c)(1),
(2) Date: Nov. 12, 2021

(87) PCT Pub. No.: WO2020/228097
PCT Pub. Date: Nov. 19, 2020

(65) Prior Publication Data
US 2022/0315623 A1 Oct. 6, 2022

(30) Foreign Application Priority Data
May 13, 2019 (CN) .......................... 201910393083

(51) Int. Cl.
| | | |
|---|---|---|
| C07K 5/062 | (2006.01) | |
| C07K 5/065 | (2006.01) | |
| C07K 5/083 | (2006.01) | |
| C07K 5/087 | (2006.01) | |
| C07K 7/06 | (2006.01) | |
| C07K 7/56 | (2006.01) | |

(52) U.S. Cl.
CPC ...... *C07K 5/06034* (2013.01); *C07K 5/06078* (2013.01); *C07K 5/0804* (2013.01); *C07K 5/0812* (2013.01); *C07K 7/06* (2013.01); *C07K 7/56* (2013.01)

(58) Field of Classification Search
None
See application file for complete search history.

(56) References Cited

FOREIGN PATENT DOCUMENTS

CN 106995483 A 8/2017

OTHER PUBLICATIONS

Li et al. ("Construction of Natural-Product-Like Cyclophane-Braced Peptide Macrocycles via sp3 C—H Arylation," J. Am. Chem. Soc. 2019, 141, 9401-9407) (Year: 2019).*
He, Gang et al, "Syntheses and Transformations of a-Amino Acids via Palladium-Catalyzed Auxiliary-Directed sp3 C—H Functionalization"; Acc. Chem. Res. vol. 49, Mar. 25, 2016, pp. 635-645.
He, Gang, et al. "Total Synthesis of Hibispeptin A via Pd-Catalyzed C(sp3)—H Arylation with Sterically Hindered Aryl Iodides"; Org. Lett. vol. 16, Dec. 9, 2014, pp. 6488-6491.
Lu, Xi, et al. "Synthesis of unnatural amino acids through palladium-catalyzed C(sp3)—H functionalization", Chinese Chemical Letters, vol. 27, Jan. 6, 2016, pp. 305-311.
Noisier, Anaïs F. M. et al, "C—H Functionalization in the Synthesis of Amino Acids and Peptides", Chemical Reviews, vol. 114, Aug. 21, 2014, pp. 8775-8806.
Tang, Jian, et al. "Synthesis of bioactive and stabilized cyclic peptides by macrocyclization using C(sp3)—H activation", Chem. Sci. vol. 8, Apr. 11, 2017, pp. 4565-4570.
Zhang, Xuekai et al. "A general strategy for synthesis of cyclophane-braced peptide macrocycles via palladium-catalysed intramolecular sp3 C—H arylation", Nature Chemistry, vol. 10, Apr. 2, 2018, pp. 540-548.

* cited by examiner

*Primary Examiner* — Christina Bradley
(74) *Attorney, Agent, or Firm* — FORGE IP, PLLC

(57) ABSTRACT

Provided are a cyclic peptide compound simulating a natural product structure and a method for preparation thereof. The method is: the compound of formula I, a divalent palladium catalyst, and a silver salt undergoing an intramolecular arylation in a solvent under heating and stirring to construct a cyclic peptide, to generate the compound of formula II, in which the arylation sites are diverse, and can be extended to the side chain γ-position methyl or methylene of the majority hydrophobic amino acids to perform intramolecular arylation, thus overcoming the previous defect of the restriction of the types of selectable amino acids, and effectively constructing a novel aromatic ring-supported cyclic peptide compound. The aromatic ring support structure forms a novel 3D structure similar to a natural product, and provide a very favorable support for the subsequent construction of a cyclic peptide molecular library and high-throughput drug screening.

13 Claims, 5 Drawing Sheets

CYCLIC PEPTIDE COMPOUND SIMULATING NATURAL PRODUCT STRUCTURE, AND METHOD FOR PREPARATION THEREOF

TECHNICAL FIELD

The present invention belongs to the field of polypeptide chemical synthesis, and specifically relates to a cyclic peptide compound that simulates the structure of a natural product and a preparation method thereof.

BACKGROUND ARTS

Nowadays, synthetic chemistry has been significantly improved for the development of small molecule drugs (MW<500D). However, chemists are very lagging behind in exploring larger "medium molecules" (500-2000D) for pharmaceutical research. This type of molecule, compared with small molecule drugs and biological drugs, accounts for a large proportion and has great potential in intervening and regulating some very difficult biological pathways, such as protein-protein interactions. In order to be able to explore this field with full freedom for drug discovery, new strategies for designing and constructing molecules with relatively large and diverse structures and biophysical properties are very necessary. Cyclic peptide compounds have a combination of various chiral building blocks and a restricted three-dimensional topological structure, thus providing a very convenient and universal platform to generate a large number of structurally diverse "medium molecules".

Many natural products in nature are cyclic peptide compounds. The linkage structure of cyclic peptide in natural products, in addition to ester bonds, amide bonds and disulfide bonds, also comprises an aromatic ring-supported cyclic peptide backbone structure. Many of cyclic peptide compounds such as hisbispetin A, celogentin C and mauritine A (as shown in FIG. 4) have good biological activity.

Such an aromatic ring-supported cyclic peptide backbone is synthesized in nature by biological pathways, usually through an enzymatic way by forming a linkage structure on the side chains having hydrophobic amino acids and aromatic amino acids via Carbon—hydrogen functionalization to construct a natural product of cyclic peptide. This relatively rigid, planar and hydrophobic linkage structure can be fully integrated into the overall backbone of the cyclic peptide to form a unique 3D support structure. Moreover, compared with weak non-covalent bond interactions, such as hydrogen-bond interaction, the aromatic ring-supported linkage structure has a more direct control over the overall polypeptide backbone, thus providing a powerful design element to help chemists create this benign cyclic peptide molecule.

However, research on the aromatic ring-supported cyclic peptide molecule is still in the initial stage. At this stage, the metal-catalyzed direct intramolecular arylation reaction also shows certain advantages to create this type of cyclic peptide molecule. The Noisier/Albericio group and the Wang Huan group have independently reported the Pd-catalyzed, polypeptide backbone-directed intramolecular arylation reaction, thus constructing the linkage structure of side chain β-methyl group of alanine with N-terminal protected by Phth and side chain benzene ring of phenylalanine. Although the advantage of this reaction is that no additional directing group is used, this reaction is limited to the composition of the polypeptide substrate and the shorter polypeptide chain length, and most substrates require the use of meta-iodo-phenylalanine with less tension to complete the linkage structure. In 2018, the inventor's research group reported a method for constructing a cyclic peptide through intramolecular arylation reaction which employs AQ as the directing group and metal Pd as the catalyst (Zhang, X.; Chen, G. Nat. Chem. 2018, 10, 540, A General Strategy for Synthesis of Cyclophane-Braced Peptide Macrocycles via Palladium-Catalyzed Intramolecular sp$^3$ C—H Arylation). This reaction can be carried out very efficiently, but the introduction of the AQ-containing alkyl chain into the polypeptide backbone can only be limited to the β-position of the carbonyl group of the linear carboxylic acid for intramolecular arylation reaction, and thus many kinds of amino acids cannot be used.

Therefore, in the synthetic construction of aromatic ring-supported cyclic peptide compounds, how to expand the reaction site of intramolecular arylation is a technical problem that needs to be solved at present.

SUMMARY OF INVENTION

An object of the present invention is to provide a cyclic peptide compound that simulates the structure of a natural product and a preparation method thereof. The cyclic peptide compound of the present invention has diverse arylation reaction sites, which can be extended to methyl or methylene on γ-position of the side chain of the most hydrophobic amino acids (amino acids connected to PA at the N-terminus), overcoming the previous defects of limited types of selectable amino acids. The method of the present invention carries out intramolecular arylation reaction at the γ-position of multiple hydrophobic amino acids at the N-terminal of the peptide chain to construct a cyclic peptide, which effectively constructs a novel aromatic ring-supported cyclic peptide compound. The aromatic ring-supported structure of such cyclic peptide can be fully integrated into the backbone of the cyclic peptide molecule to form a novel 3D structure similar to natural products (hisbispetin A, celogentin C and mauritine A), and has good rigidity and complex stereochemical structure. This provides a very favorable support for the subsequent construction of cyclic peptide library and high-throughput drug screening.

In order to achieve the above objectives, the present invention adopts the following technical solutions:

A precursor of cyclic peptide compound simulating natural product structure, having general structural formula I,

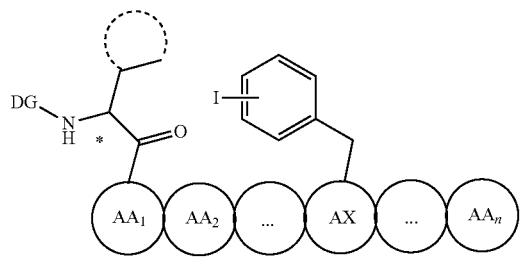

Formula I wherein DG is a directing group; AA$_1$ to AA$_n$ represent a peptide chain, n represents length of the peptide chain, and the value range of n is 3-10; wherein a peptide chain segment corresponding to AA$_3$ to AA$_n$ contains at least one aryl iodide side chain, and the part containing the aryl iodide side chain in the peptide chain segment is denoted as AX; * is a chiral center and

represents a alkyl side chain. It should be noted that AX in the above general formula refers to the overall structure containing the aryl iodide side chain, as shown in FIG. 6.

In a preferred embodiment of the above technical solution, AX in the peptide chain is one or more selected from the group consisting of 3-iodophenylalanine, 3-iodotyrosine, 3-iodo-p-methoxyphenylalanine, 4-iodophenylalanine and a compound formed by assembling aryl iodobenzene on the side chain of lysine, serine, or glutamic acid. (The method for assembling aryl iodobenzene on the side chain of lysine, serine, glutamic acid can be referred to: Zhang, X.; Chen, G. Nat. Chem. 2018, 10, 540; A General Strategy for Synthesis of Cyclophane-Braced Peptide Macrocycles via Palladium-Catalyzed Intramolecular sp$^3$ C—H Arylation).

In a preferred embodiment of the above technical solution, AX is located at the end of the peptide chain segment corresponding to $AA_3$ to $AA_n$.

In a preferred embodiment of the above technical solution, AX also includes 3-iodobenzylamine or 3-iodophenethylamine.

In a preferred embodiment of the above technical solution, the amino acids other than AX in the peptide chain are selected from the group consisting of α-amino acids, 3-aminopropionic acid, 4-aminobutyric acid, 5-aminovaleric acid, 6-aminobutyric acid, 7-aminoheptanoic acid and 8-aminooctanoic acid.

In a preferred embodiment of the above technical solution, the α-amino acid is selected from the group consisting of glycine, alanine, proline, N-Me-alanine, 2-aminobutyric acid, 2-aminopentanoic acid, valine, isoleucine, leucine, tert-leucine, phenylalanine, threonine, serine, lysine, arginine, glutamic acid, glutamine, aspartame acid, asparagine, tryptophan, cysteine, methionine, tyrosine, histidine and cyclohexylglycine.

In a preferred embodiment of the above technical solution, the alkyl side chain is selected from the group consisting of ethyl, propyl, isopropyl, isobutyl, cyclopropyl, cyclobutyl, cyclopentyl, cyclohexyl, allyl and phenyl.

In a preferred embodiment of the above technical solution, DG is any one selected from the group consisting of the following groups:

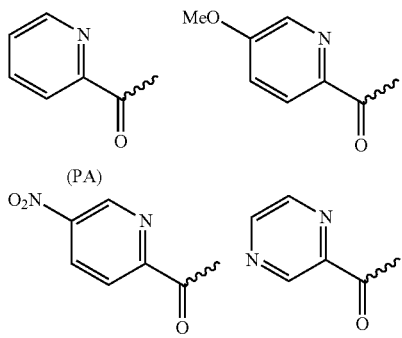

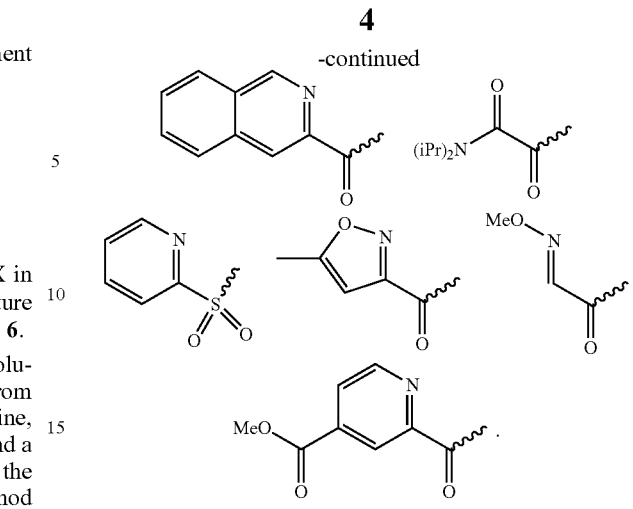

Among the directing group disclosed by the present invention, the effect of PA is the best. The action principle of PA is bidentate coordination metal Pd, so as to carry out C—H activation. The action principle of the above-mentioned directing group is the same as that of PA for bidentate guiding intramolecular arylation, and all can realize the construction of cyclic peptides.

The specific structure of the precursor of the cyclic peptide compound of the present invention is shown in FIG. 1.

The present invention also provides a cyclic peptide compound having general structural formula II, which is prepared by an intramolecular arylation reaction from the precursor of the cyclic peptide compound

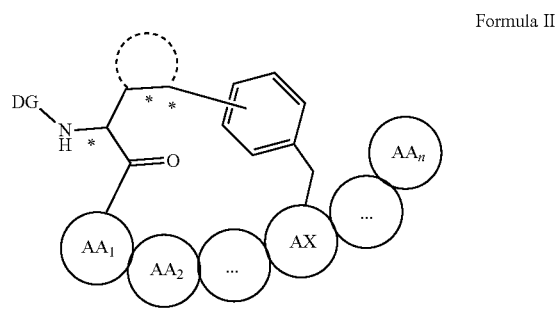

Formula II wherein the peptide chain structure of the cyclic peptide compound corresponds to the peptide chain structure of the precursor thereof.

In a preferred embodiment of the above technical solution, the cyclic peptide compound has a specific structure showed in FIG. 2.

The present invention also provides a method for preparing a cyclic peptide compound simulating the structure of a natural product, comprising the following steps: subjecting a compound of formula I, a divalent palladium catalyst, and a silver salt to intramolecular arylation reaction under heating and stirring in a solvent to construct a cyclic peptide to produce a compound of formula II.

In a preferred embodiment of the above preparation method, the concentration of the compound of formula I in the solvent is 50-200 mM, and the molar ratio of the compound of formula I:the divalent palladium catalyst: the silver salt is 1:0.05-0.15:1.5-3.0.

In a preferred embodiment of the above preparation method, the solvent is any one selected from the group consisting of hexafluoroisopropanol, chlorobenzene, trifluoroethanol, dichloroethane, tert-amyl alcohol, water, and a mixed solvent of hexafluoroisopropanol and water at a volume ratio of 1:0-1:2.

In a preferred embodiment of the above preparation method, the divalent palladium catalyst is one selected from the group consisting of $Pd(CH_3CN)_4(BF_4)_2$, $Pd(OAc)_2$, $Pd(TFA)_2$, $Pd(OPiv)_2$ and $Pd(CH_3CN)_2Cl_2$; and the silver salt is one selected from the group consisting of silver acetate, silver benzoate, silver carbonate, silver oxide and silver phosphate.

In a preferred embodiment of the above preparation method, the reaction conditions of the intramolecular arylation reaction includes a heating temperature of 110-130° C. and a reaction time of 6-48 hours.

The reaction principles of the present invention are as follows.

The previous work of the research group of the present invention was to introduce an alkyl side chain containing an AQ directing group as arylation site, which reduces the difficulty of intramolecular ring closure. Because this alkyl chain is far away from the peptide backbone, and the coordination of Pd and AQ is not affected by the amide bond on the peptide backbone, the intramolecular arylation proceeds smoothly.

The present invention uses the side chain of the polypeptide backbone as a reaction site. When the PA-directing group is arylated on the amino acid side chain, the coordination site uses the PA itself and the N atom of the first amino acid on the polypeptide. The coordination takes place in the polypeptide backbone, and the amide bond itself on the polypeptide backbone has the ability to coordinate with the metal Pd. Therefore, the introduced directing group competes with the metal amide bond to bind metal Pd and then arylation reaction occurs. The PA directing group is greatly interfered by other amide bonds on the polypeptide.

The present invention utilizes the strategy of directing group to coordinate with metal Pd at a fixed site and to perform C—H activation reaction so as to generate intramolecular arylation reaction which constructs a cyclic peptide. In the present invention, PA is used as the directing group, and its coordination ability is stronger than the amide bond. When PA-directed intramolecular arylation is carried out, compared with AQ, the arylation reaction sites are diverse, thereby forming a variety of cyclic peptide backbones with different supporting structures.

In these amino acids with arylation sites, the difficulty of ring closure of side chain alkyl is as follows:

isopropyl $(CH_3)$>cyclopropyl $(CH_2)$>isobutyl $(CH_3)$>phenyl (CH) cyclopentyl $(CH_2)$>cyclohexyl $(CH_2)$>ethyl $(CH_3)$>propyl $(CH_2)$.

The intramolecular arylation process according to the present invention is as follows: the divalent palladium metal is first coordinated with PA, followed by hydrocarbon activation to form a 5-5 fused bicyclo palladium intermediate, which further undergoes oxidative addition with the arylioidide part to form a tetravalent palladium intermediate, and finally reduction and elimination occurs to obtain an intramolecular arylation product. The whole cycle is relatively smooth with a good yield, so no additives are needed to promote the reaction.

The intramolecular arylation reaction according to the present invention can be carried out in water. It is speculated that water as a solvent may not participate in the cycle of divalent palladium and tetravalent palladium, and the weak acidity of water weakens the coordination ability of the free amino group and the carboxyl group to the palladium, so as to promote the PA-directed C—H arylation reaction, while the existing intramolecular arylation reaction cannot proceed in water substantially.

The PA directing group according to the present invention is significantly different from AQ mentioned in the background art in the aspects of directing process and removal;

AQ (8-amino-quinoline) mentioned in the background art (Zhang, X.; Chen, G. Nat. Chem. 2018, 10, 540; A General Strategy for Synthesis of Cyclophane-Braced Peptide Macrocycles via Palladium-Catalyzed Intramolecular sp$^3$ C—H Arylation) is more expensive, and needs to undergo a condensation reaction with the carboxyl group when playing the role of directing group (due to the weak nucleophilicity of the amino group on AQ, a more active condensing agent is required to react with the carboxyl group), and the C—H functionalization reaction is usually carried out at $CH_2$ or $CH_3$ of the β-position of the carboxyl group. PA (2-picolinic acid) is commercially available and very cheap. When PA plays the role of directing group, it needs to undergo a condensation reaction with the amino part, and the C—H functionalization reaction is usually carried out at $CH_3$ or $CH_2$ on γ-position of the amino group. Although there are some reported methods for the removal of AQ, AQ in the peptide system cannot be removed by the reported methods. It can only be removed after AQ is converted to MQ, and the removal efficiency is not high. However, PA can be removed quickly and efficiently at room temperature using zinc and dilute hydrochloric acid, which is also suitable for peptide systems. Therefore, due to the high efficiency of PA, it can basically be regarded as a protecting group strategy in peptide chemistry.

Beneficial Effects

1. At present, the strategy for constructing aromatic ring-supported cyclic peptide by using C—H activation strategy has a limitation in that a majority of them can only carry out intramolecular arylation reactions at β-position methyl or methylene of alanine or phenylpropanine, and are also relatively restricted in size and amino acid composition of the cyclic peptide. In addition, introduction of an alkyl chain containing AQ into the polypeptide backbone can only be restricted in intramolecular arylation at β-position of the carbonyl group of linear carboxylic acid, making many kinds of amino acids unavailable. For the cyclic peptide compound of the present invention, the arylation sites are diverse and the intramolecular arylation can occur on γ-position methyl or methylene of most hydrophobic amino acids (amino acids connected to PA at the N-terminus), overcoming the previous defects of the limited selection of selectable amino acid types. Also, For the cyclic peptide compound of the present invention, the size of the cyclic peptide chain can vary from tripeptide to decapeptide, and the composition of amino acids in the polypeptide chain covers almost all types, including hydrophobic and hydrophilic amino acids, thus greatly broadening the application range of carbon-hydrogen activation, which proves that C—H functionalization can still proceed in the presence of interfering polar groups. Thus the types of amino acids are no longer limited, and there is a broader selection of groups for future active drug molecule screening. The permutation and combination of various amino acids with different properties will create a larger library of cyclic peptide molecules. In addition, the diverse aryl-coupling parts result in the diverse backbones of the cyclic peptides, enriching the 3D structure of the cyclic peptides, which provides possibility for discovery of the polypeptide stereo-structures efficiently binding with proteins. The cyclic peptide structure formed is more rigid and has a more complex stereo-chemical structure.

2. In the present invention, the ring-closure product after intramolecular arylation reaction has a new chirality, which makes the stereo-chemical structure of the cyclic peptide molecule more complicated. The natural product molecules in nature have abundant and complex chiral centers. The cyclic peptides created by the present invention can be closer to the characteristics of molecules created in nature. Furthermore, the more chiral centers in the molecule, the more complex of the stereo-chemical structure, and the more possible for standing out in the drug screening process.

3. The raw material of the cyclic peptide compound of the present invention (precursor linear peptide, that is, the compound of formula I) is simple and efficient to prepare, using classic solid-phase peptide synthesis methods. Most of the substrates can be obtained through this strategy, and can be directly subjected to the next reaction without any purification, which saves time, has good yield and high purity, and overcomes the cumbersome defects of raw material preparation in liquid phase synthesis of peptides.

4. The preparation process of the cyclic peptide compound of the present invention can not only be carried out in an organic solvent, but also can be carried out in water as a solvent. Amino acids with polar side chains, such as lysine, serine, arginine, threonine, glutamic acid, glutamine, etc., without protection or additional additives, can be subjected to intramolecular arylation reaction using water as a solvent. The reaction process is more environmental, simple and efficient. This strategy not only proves the effectiveness of Pd-catalyzed hydrocarbon activation, but also provides a very good orthogonal reaction strategy for peptide chemistry.

5. In the synthesis of the cyclic peptide compound of the present invention, the directing group PA not only serves as a directing group in the reaction system, but also used as a protecting group and serves as a modified group on the N-terminus of peptides in peptide chemistry for active drug molecule screening since removal of PA is very simple and efficient.

DETAILED EMBODIMENTS

The present invention will be further described through the following embodiments.

I. Preparation of the Ring-Closure Precursor Linear Peptide (i.e. the Compound of Formula I)

Figure 8:
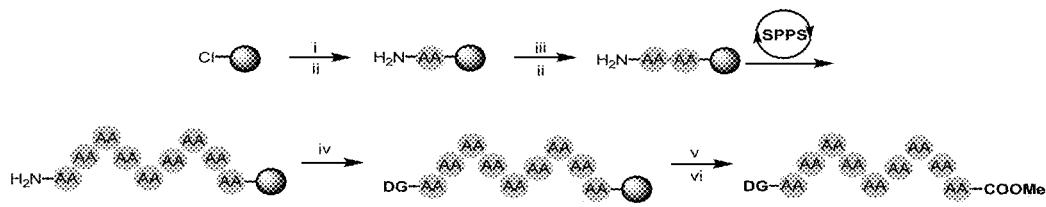
FIG. 8 shows the reaction route of general preparation method 1.

General preparation method 1 (as shown in FIG. 8): Preparation of the linear peptide with methyl ester at C-terminus (Albericio, F. Angew. Chem., Int. Ed. 2017, 56, 314, Stapled Peptides by Late-Stage C(sp3)-H Activation.)

i) Loading of 2-Cl-trt resin; ii) Removal of Fmoc protecting group; iii) Amino acid condensation; iv) Condensation of directing group to N-terminus; v) Cleavage from 2-Cl-trt resin; vi) Methyl esterification of C-terminus.

i) Loading of 2-Cl-trt resin: 2-Cl-trt resin was weighed in a solid phase synthesis tube, 5% DIPEA/DCM solution was added to swell the resin for 10 minutes, and then the solvent was pumped dry. Fmoc-AA-OH (1.2 equiv) and DIPEA (6.0 equiv) were then dissolved in DCM, the solution was clarified, and then added to the solid phase synthesis tube and mixed evenly with the resin. The reaction was performed under shaking at room temperature for 1.5 hours, and then the reaction solvent was pumped dry and the residue was washed twice with DMF and DCM respectively for the next reaction.

ii) Removal of Fmoc protecting group: 20% piperidine/DMF was added to the solid phase synthesis tube, shook for reaction for 10 minutes, and then the reaction solvent was pumped dry. The residue was washed twice with DMF and DCM respectively. The above operation was repeated to complete the removal of the Fmoc protecting group.

iii) Amino acid condensation: Fmoc-AA-OH (3.0 equiv) and ethyl cyanoglyoxylate-2-oxime (3.0 equiv) were dissolved in NMP to make a clarified solution, and then DIC (3.3 equiv) was added and reacted for 5 minutes in an ice-water bath. Subsequently, the reaction solution was added to the solid phase synthesis tube to react for 1.5 hours at room temperature. Then the reaction solvent was pumped dry and the residue was washed twice with DMF and DCM respectively for the following deprotection procedure.

iv) Condensation of directing group to N-terminus: Take 2-picolinic acid (PA-COOH) for an example, PA-COOH (3.0 equiv) and ethyl cyanoglyoxylate-2-oxime (3.0 equiv) were dissolved in NMP to make a clarified solution, and then DIC (3.3 equiv) was added therein and reacted for 5 minutes at room temperature. Subsequently, the reaction solution was added to the solid phase synthesis tube to react for 1.5 hours at room temperature. Then the reaction solvent was pumped dry and the residue was washed twice with DMF, DCM and Et₂O respectively. The resin was air-dried at room temperature.

v) Cleavage from 2-Cl-trt resin: Trifluoroethanol, acetic acid and dichloromethane were mixed in a volume ratio of 1:1:3 to prepare a cleavage solution. The cleavage solution was then added into the solid phase synthesis tube to react for 1.0 hour, and the liquid phase was then separated and collected. Another cleavage solution was added into the solid phase synthesis tube to react for 1.0 hour, and then the liquid phase was collected again. The two liquid phases were combined and the solvent was evaporated and pumped dry to give a crude peptide with free carboxyl group at the C-terminus.

vi) Methyl esterification of C-terminus: The peptide with free carboxyl group at the C-terminus was dissolved in anhydrous methanol, and then thionyl chloride (5.0 equiv) was added therein slowly in an ice-water bath. The mixture was slowly warmed to room temperature and continuously reacted for 3 hours with the reaction monitored by LCMS during the process. After the reaction, the solvent was evaporated and the methyl esterification product was obtained, which was then extracted with ethyl acetate, washed twice with saturated sodium bicarbonate, then washed twice with saturated saline and dried over anhydrous sodium sulfate. After ethyl acetate was evaporated, the final product was obtained.

Figure 9:
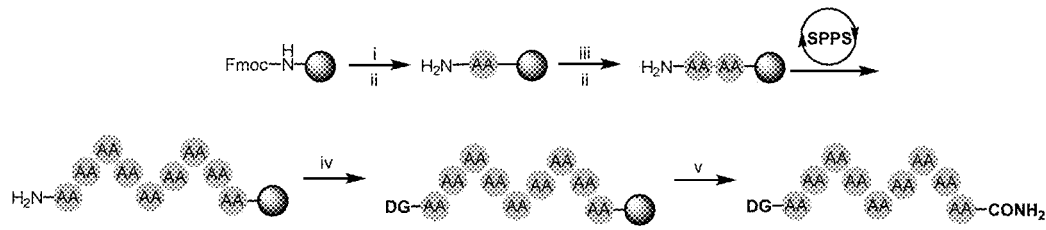
FIG. 9 shows the reaction route of general preparation method 2.

General preparation method 2 (as shown in FIG. 9): Preparation of the linear peptide with amide at C-terminus (Albericio, F. Angew. Chem., Int. Ed. 2017, 56, 314.)

i) Rink-Amide-AM resin; ii) Removal of Fmoc protecting group; iii) Amino acid condensation; iv) Condensation of directing group at N-terminus; v) Cleavage from Rink-Amide-AM resin.

The steps of ii, iii and iv are the same as the above mentioned;

v) Cleavage from Rink-Amide-AM resin: A cleavage solution made of trifluoroacetic acid and water in a volume ratio of 95:5 was added to the solid phase synthesis tube to react for 2.0 hours at room temperature. Then the liquid phase was collected and the solvent was removed. Ether was added to the residue for precipitating the peptide, which was then centrifuged to give a crude peptide with amide at the C-terminus.

The crude peptide with amide at the C-terminus prepared by the above method has a high basic purity and can be used in the subsequent synthesis of cyclic peptide compounds.

Purification can be made when necessary by the preparative HPLC method in the prior art.

Figure 10:
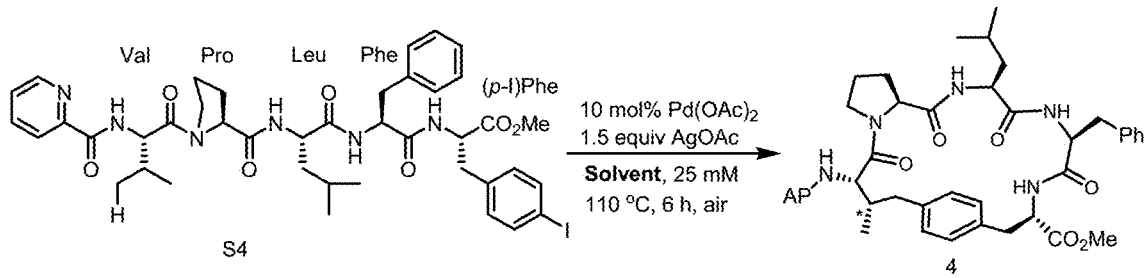
FIG. 10 shows the reaction route in Examples 1-9.

II. The Cyclic Peptide Compounds of the Present Invention and the Preparation Method Thereof Examples 1-9: Screening of Reaction Solvents The reaction route is shown in FIG. 10.

The linear peptide (serial No. S4) (43.4 mg, 0.05 mmol, 1.0 equiv), AgOAc (12.6 mg, 0.075 mmol, 1.5 equiv) and Pd(OAc)₂ (2.2 mg, 10 mol %) was weighed in an 8 mL reaction flask (sealed with a PTFE lid), then 2 mL solvent was added at room temperature and stirred for 5 minutes. The mixture was heated to 110° C. for 6 hours for reaction. The reaction solution was cooled to room temperature, diluted with 5 mL acetone, and filtered with diatomaceous earth. The filtrate obtained was evaporated to obtain an oily substance, which was purified by column chromatography to obtain the final white ring-closure product. The difference between Examples 1-9 only lies in the reaction solvent, as shown in Table 1 for detail.

TABLE 1

Screening of reaction solvent

| Example | Solvent | Yield |
|---|---|---|
| 1 | PhCl | 43 |
| 2 | DMF | 15 |
| 3 | H2O | <5 |
| 4 | t-AmylOH | 29 |
| 5 | DCE | 40 |
| 6 | HFIP | 55 |
| 7 | AcOH | <5 |
| 8 | PhMe | 17 |
| 9 | 1,4-dioxane | 19 | a: LCMS Yield

It can be seen from the results of the examples 1-9 that when HFIP was chosen as the solvent, the yield was higher.

Examples 10-16: Screening of Divalent Palladium Metal Catalysts

Figure 11:
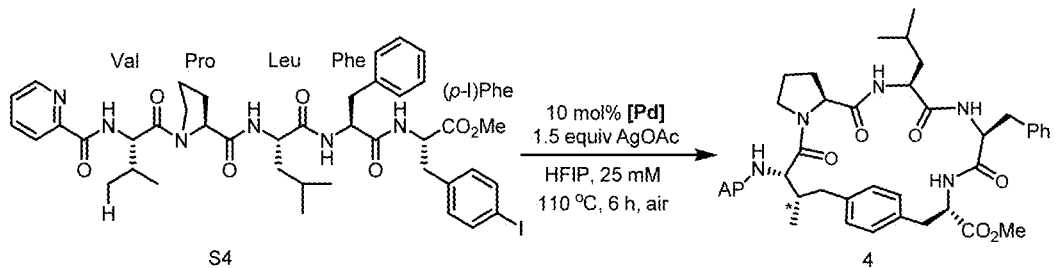
FIG. 11 shows the reaction route in Examples 10-16.

Reaction route is shown in FIG. 11.

The preparation methods of examples 10-16 were almost the same as that of example 6, only differing in the divalent palladium metal catalyst, as shown in Table 2 for detail.

| Example | [Pd] | Yield (%)$^a$ |
|---|---|---|
| 10 | Pd(TFA)₂ | 57 |
| 11 | Pd(PPh₃)₂Cl₂ | 36 |
| 12 | Pd(CH₃CN)₂Cl₂ | 42 |
| 13 | Pd(PhCN)₂Cl₂ | 56 |
| 14 | Pd(CH₃CN)₄(BF₄)₂ | 73 |
| 15 | PdBr | 17 |
| 16 | Pd(OPiV)₂ | 58 |

$^a$LCMS Yield

It can be seen from the results of the examples 10-16 that when Pd(CH₃CN)₄(BF₄)₂ was chosen as the palladium metal catalyst, the yield was higher.

Examples 17-24: Screening of Silver Salts

Figure 12:
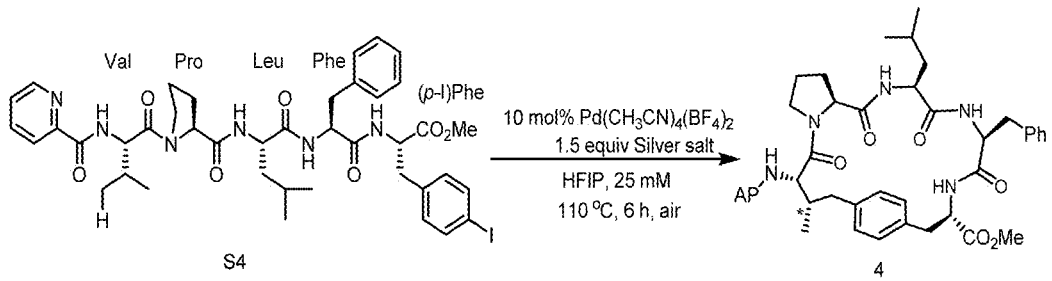
FIG. 12 shows the reaction route in Examples 17-24.

Reaction route is shown in FIG. 12.

The preparation methods of examples 17-24 were almost the same as that of example 14, only differing in the silver salts, as shown in Table 3 for detail.

TABLE 3

Screening of silver salts

| Example | Silver salt | Yield (%)$^a$ |
|---|---|---|
| 17 | AgTFA | 6 |
| 18 | AgOTf | 8 |
| 19 | AgNO₃ | 18 |
| 20 | AgF | 8 |
| 21 | Ag₂O | 10 |
| 22 | PhCOOAg | 60 |

TABLE 3-continued

Screening of silver salts

| Example | Silver salt | Yield (%)[a] |
|---|---|---|
| 23 | $Ag_2CO_3$ | 10 |
| 24 | $Ag_3PO_4$ | 17 |

[a]LCMS Yield

It can be seen from the results of the examples 17-24 that when AgOAc in example 14 was chosen as the silver salt, the yield was higher.

Examples 25-29: Screening of Additives

Figure 13:
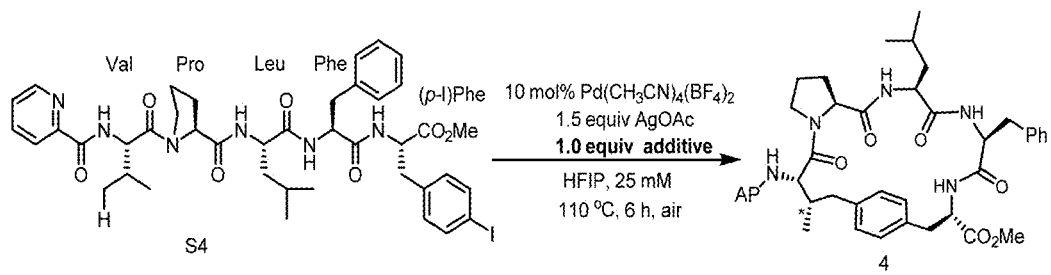
FIG. 13 shows the reaction route in Examples 25-29.

Reaction route is shown in FIG. 13.

The preparation methods of examples 25-29 were almost the same as that of example 14, only differing in the additives, as shown in Table 4 for detail.

TABLE 4

Screening of additives

| Example | Additive | Yield (%)[a] |
|---|---|---|
| 25 | o-PBA | 59 |
| 26 | BP acid | 20 |
| 27 | 1-Ad-COOH | 56 |
| 28 | PivOH | 53 |
| 29 | TsOH•$H_2O$ | 55 |

[a]LCMS Yield

It can be seen from the results of the examples 25-29 that the yield of example 14, in which no additive was used, was higher.

Figure 14:
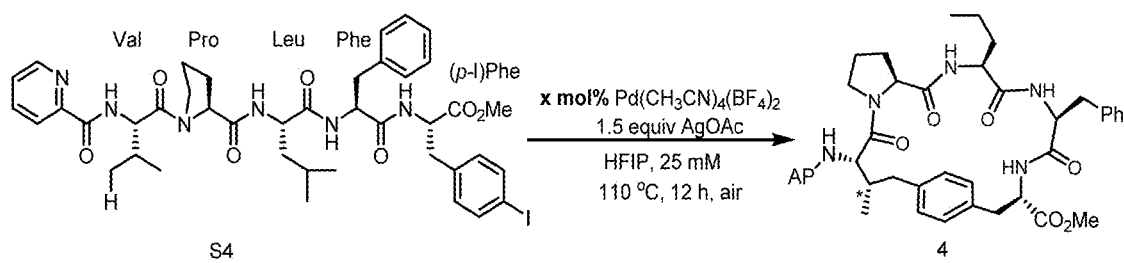
FIG. 14 shows the reaction route in Examples 30-33.

Examples 30-33: Screening of the Concentration of $Pd(CH_3CN)_4(BF_4)_2$ Catalyst Reaction route is shown in FIG. 14.

The preparation methods of examples 30-33 were almost the same as that of example 14, only differing in that the concentration of $Pd(CH_3CN)_4(BF_4)_2$ chosen by examples 30-33 was different and the reaction time was extended to 12 hours, as shown in Table 5 for detail.

TABLE 5

Screening of the concentration of $Pd(CH_3CN)_4(BF_4)_2$ catalyst

| Example | Concentration of catalyst (%) | Yield (%)[a] |
|---|---|---|
| 30 | 2.5 | 41 |
| 31 | 5 | 57 |

TABLE 5-continued

Screening of the concentration of $Pd(CH_3CN)_4(BF_4)_2$ catalyst

| Example | Concentration of catalyst (%) | Yield (%)[a] |
|---|---|---|
| 32 | 7.5 | 71 |
| 33 | 10 | 83(76)[b] |

[a]LCMS Yield at 12 h
[b]isolated yield

It can be seen from the results of the examples 30-33 that the yield of example 33, with the concentration of $Pd(CH_3CN)_4(BF_4)_2$ being 10 mol %, was higher.

Examples 34-37: Screening of Reactant Concentration

Figure 15:
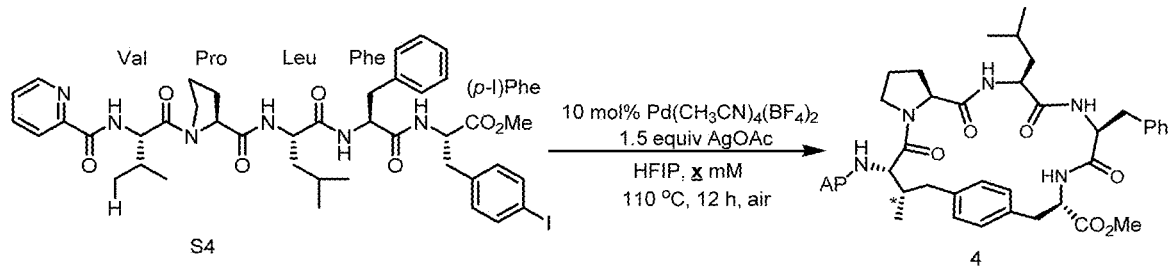
FIG. 15 shows the reaction route in Examples 34-37.

Reaction route is shown in FIG. 15.

The preparation methods of examples 34-37 were almost the same as that of example 33, only differing in the reactant concentration, as shown in Table 6 for detail.

TABLE 6

Screening of HFIP concentration

| Example | x (mM) | Yield (%)[a] |
|---|---|---|
| 34 | 50 | 82 |
| 35 | 100 | 72 |
| 36 | 150 | 40 |
| 37 | 200 | 33 |

[a]LCMS Yield at 12 h

It can be seen from the results of the examples 34-37 that the yield of example 37, with 200 nM HFIP being added, was higher.

Examples 38-75

Figure 1:
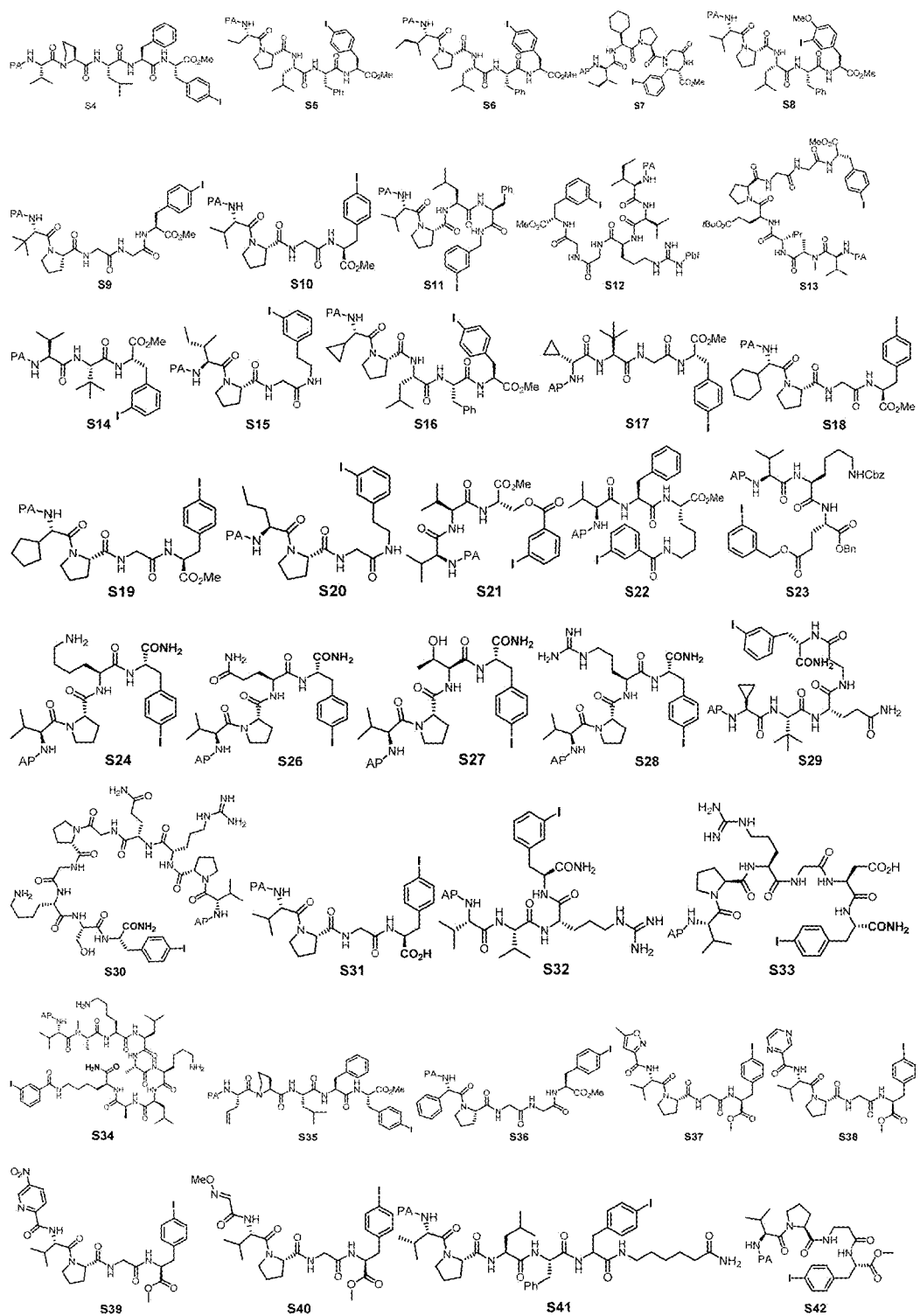
FIG. 1 shows the structural formula of the specific compound corresponding to the compound of general formula I (precursor of cyclic peptide compound) of the present invention.
Figure 2:
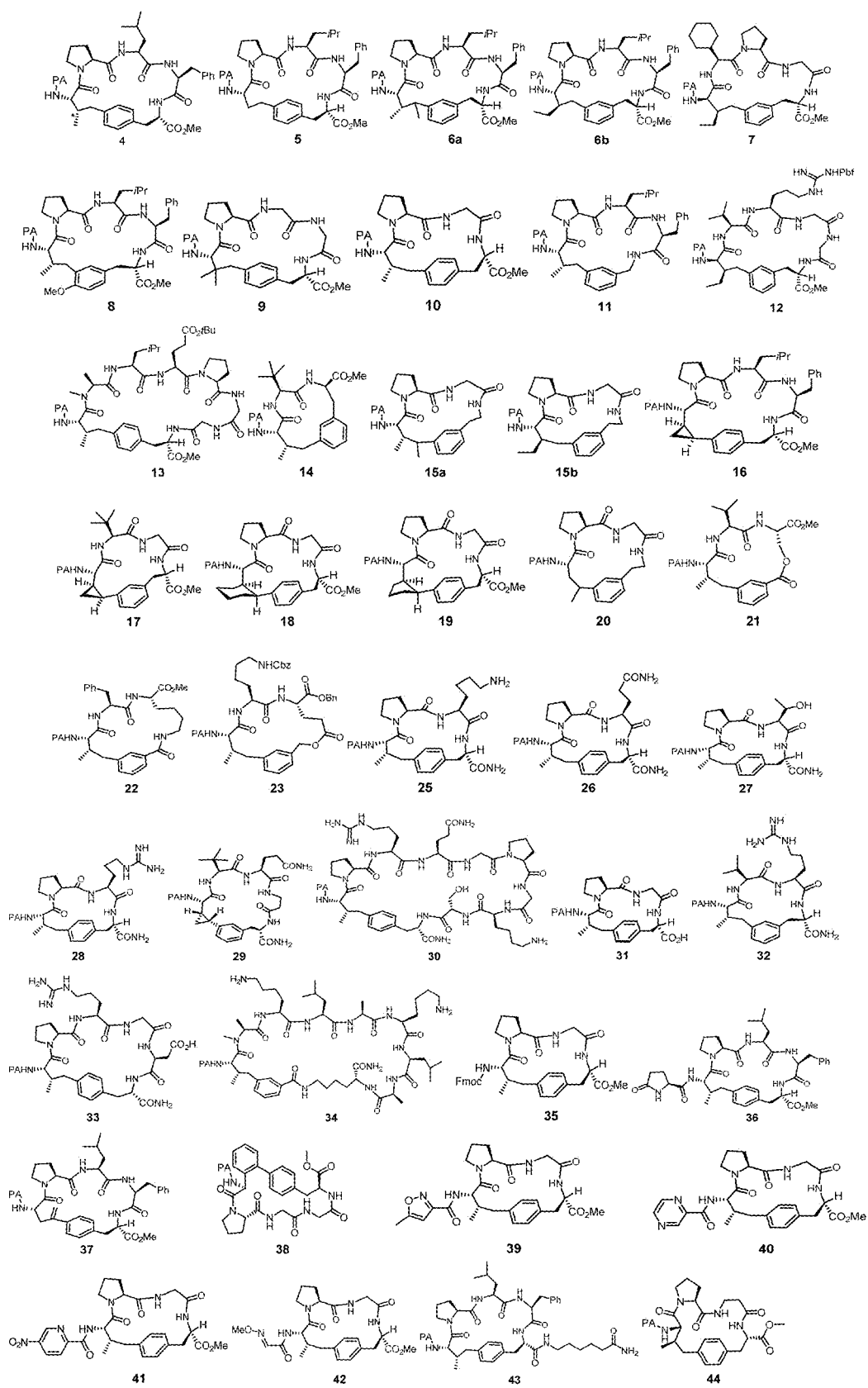
FIG. 2 shows the structural formula of the specific compound corresponding to the compound of general formula II (cyclic peptide compound) of the present invention.
Figure 3:
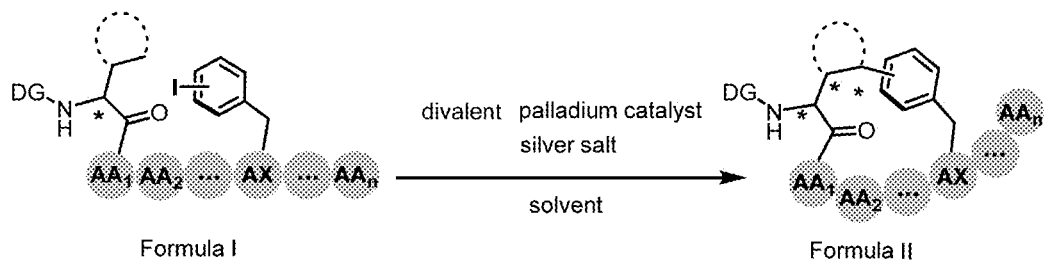
FIG. 3 shows the reaction equation of the compound of formula I to the compound of formula II.
Figure 4:
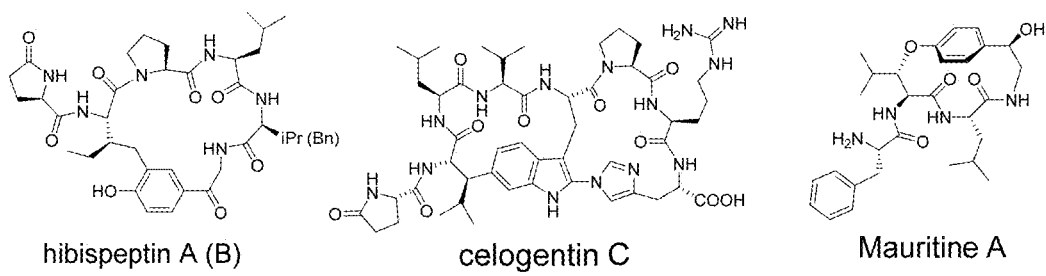
FIG. 4 shows the structures of hisbispetin A, celogentin C, and mauritine A.
Figure 5:
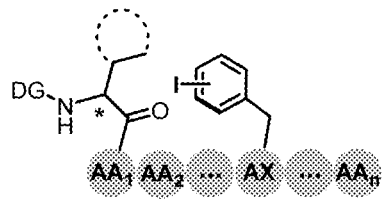
FIG. 5 shows the general formula I of the precursor of cyclic peptide compound.
Figure 6:
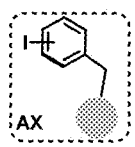
FIG. 6 shows the structure of AX.
Figure 7:
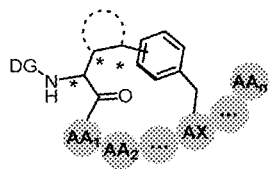
FIG. 7 shows the general formula II of the cyclic peptide compound.

The compound of formula I (43.4 mg, 0.05 mmol, 1.0 equiv), AgOAc (12.6 mg, 0.075 mmol, 1.5 equiv) and $Pd(CH_3CN)_4(BF_4)_2$ (2.2 mg, 10 mol %) were weighed in 8 mL reaction flask (sealed with a PTFE lid), and then 2 mL solvent was added at room temperature, followed by stirring for 5 minutes. The mixture was then heated to 110-130° C. for 12-48 hours for reaction. The reaction solution was cooled to room temperature, diluted with 5 mL acetone, and filtered with diatomaceous earth. The filtrate obtained was evaporated to obtain an oily substance, which was purified by column chromatography to give the final ring-closure product. The specific choices of the compounds of formula I and the reaction conditions in examples 38-75 are shown in Table 7, wherein the compounds of formula I were showed in FIG. 1, the compounds of formula II were showed in FIG. 2, and the general equation for the reaction from compounds of formula I to compounds of formula IL was showed in FIG. 4.

TABLE 7

Reaction conditions of examples 38-75

| Example | compounds of formula I (Serial No.) | Solvent | Reaction temperature/° C. | Reaction time/h | compounds of formula II (Serial No.) | Yield/% |
|---|---|---|---|---|---|---|
| 38 | S4 | HFIP | 110 | 12 | 4 | 76 |
| 39 | S5 | HFIP | 130 | 48 | 5 | 61 |

TABLE 7-continued

Reaction conditions of examples 38-75

| Example | compounds of formula I (Serial No.) | Solvent | Reaction temperature/° C. | Reaction time/h | compounds of formula II (Serial No.) | Yield/% |
|---|---|---|---|---|---|---|
| 40 | S6 | HFIP | 110 | 12 | 6a + 6b | 49 + 24 |
| 41 | S7 | HFIP | 110 | 24 | 7 | 65 |
| 42 | S8 | HFIP | 130 | 48 | 8 | 41 |
| 43 | S9 | HFIP | 120 | 48 | 9 | 27 |
| 44 | S10 | HFIP | 110 | 12 | 10 | 78 |
| 45 | S11 | HFIP | 110 | 12 | 11 | 62 |
| 46 | S12 | HFIP | 110 | 24 | 12 | 46 |
| 47 | S13 | DCE | 110 | 12 | 13 | 61 |
| 48 | S14 | HFIP | 110 | 12 | 14 | 80 |
| 49 | S15 | HFIP | 110 | 12 | 15a + 15b | 30 + 39 |
| 50 | S16 | HFIP | 110 | 12 | 16 | 75 |
| 51 | S17 | HFIP | 110 | 12 | 17 | 66 |
| 52 | S18 | HFIP | 120 | 24 | 18 | 50 |
| 53 | S19 | HFIP | 120 | 24 | 19 | 51 |
| 54 | S20 | HFIP | 130 | 48 | 20 | 31 |
| 55 | S21 | HFIP | 120 | 12 | 21 | 57 |
| 56 | S22 | HFIP | 110 | 12 | 22 | 73 |
| 57 | S23 | HFIP | 130 | 12 | 23 | 51 |
| 58 | S24 | $H_2O$ | 110 | 12 | 25 | 65 |
| 59 | S26 | $H_2O$ | 110 | 12 | 26 | 69 |
| 60 | S27 | $H_2O$ | 110 | 12 | 27 | 41 |
| 61 | S28 | $H_2O$/HFIP | 110 | 12 | 28 | 66 |
| 62 | S29 | $H_2O$/HFIP | 110 | 12 | 29 | 47 |
| 63 | S30 | $H_2O$ | 110 | 12 | 30 | 59 |
| 64 | S31 | $H_2O$/HFIP | 110 | 12 | 31 | 71 |
| 65 | S32 | $H_2O$/HFIP | 120 | 24 | 32 | 67 |
| 66 | S33 | $H_2O$/HFIP | 110 | 12 | 33 | 46 |
| 67 | S34 | $H_2O$ | 110 | 12 | 34 | 72 |
| 68 | S35 | HFIP | 110 | 12 | 37 | 55 |
| 69 | S36 | HFIP | 120 | 12 | 38 | 47 |
| 70 | S37 | HFIP | 110 | 12 | 39 | 37 |
| 71 | S38 | HFIP | 110 | 12 | 40 | 15 |
| 72 | S39 | HFIP | 110 | 12 | 41 | 16 |
| 73 | S40 | HFIP | 110 | 12 | 42 | 19 |
| 74 | S41 | HFIP | 110 | 12 | 43 | 76 |
| 75 | S42 | HFIP | 110 | 12 | 44 | 78 |

The molar ratio of $H_2O$ to HFIP in the mixed solvent used in Examples 61 and 64 of the present invention is 9:1, and the molar ratio of $H_2O$ to HFIP in the mixed solvent used in Examples 62, 65, and 66 is 1:2.

The directing groups of the present invention have the same principle of action as PA, which is bidentate-directed intramolecular arylation, and all the directing groups can realize the construction of cyclic peptides. Among the directing groups of the present invention, PA has the best effect.

III. Removal of PA-Directing Group in the Product

Example 76

Figure 16:
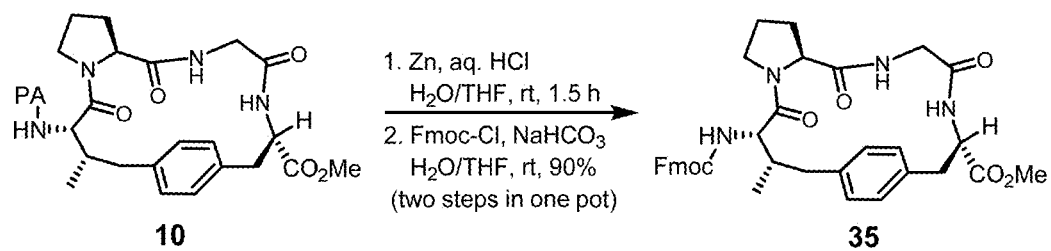
FIG. 16 shows the reaction route of Examples 76.

The reaction route is shown in FIG. 16.

The product 10 (53.5 mg, 0.1 mmol, 1.0 equiv) was dissolved in THF/$H_2O$ (2:1, v/v) and stirred at room temperature, hydrochloric acid solution (1.5M, 1 mL) was slowly added therein, and then zinc powder (98.1 mg, 1.5 mmol, 15.0 equiv) was added. The mixture was stirred for 1.5 h at room temperature. After the completion of the reaction of the raw materials as monitored by TLC, $NaHCO_3$ was added to adjust pH to 7-8, and then Fmoc-Cl (77.6 mg, 0.3 mmol, 3.0 equiv) was added, and reacted for 6 hours at room temperature. Then an appropriate amount of water was added to the system, which was then extracted three times with ethyl acetate. The organic phases were combined, washed twice with saturated saline, and dried over anhydrous sodium sulfate. After ethyl acetate was evaporated, the crude product was obtained, which was purified by column chromatography to obtain product 35 (58.7 mg, 90%).

Example 77

Figure 17:
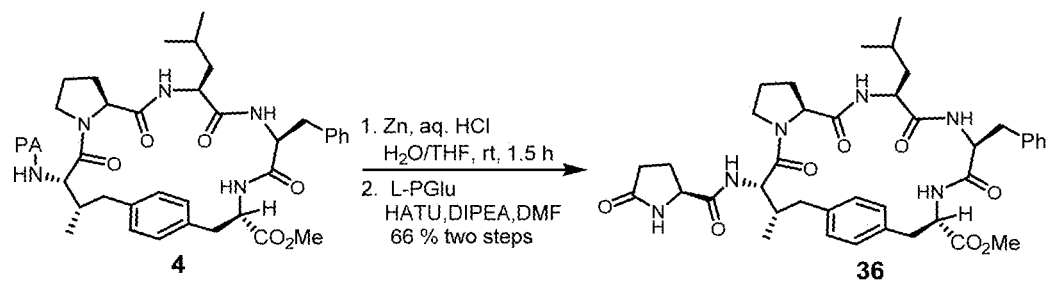
FIG. 17 shows the reaction route of Examples 77.

The reaction route is shown in FIG. 17.

The method for removing PA in Example 77 was almost the same as that of example 76, differing in that after removal of the directing group PA, product 4 was subjected to a further condensation reaction with L-pyroglutamic acid so as to obtain product 36.

IV. Characterization of Product Structure

The test datas of products 4-42 are as follows:

Product 4

HRMS: Calcd for $C_{41}H_{50}N_6NaO_7$ [M+Na$^+$]:761.3633; found: 761.3633.

$^1$H NMR (400 MHz, CDCl$_3$) δ 8.68 (d, J=7.8 Hz, 1H), 8.60 (d, J=4.2 Hz, 1H), 7.68 (t, J=7.4 Hz, 1H), 7.62 (d, J=7.6 Hz, 1H), 7.43 (d, J=5.6 Hz, 2H), 7.24-7.12 (m, 5H), 6.92-6.80 (m, 3H), 6.65 (d, J=5.2 Hz, 3H), 5.03 (t, J=8.4 Hz, 1H), 4.69 (s, 1H), 4.13-4.05 (m, 1H), 4.00 (t, J=9.2 Hz, 1H), 3.84 (d, J=6.2 Hz, 1H), 3.70 (s, 3H), 3.66-3.60 (m, 1H), 3.56 (d, J=13.6 Hz, 1H), 3.33 (dd, J=13.6, 5.2 Hz, 1H), 3.15-2.94 (m, 4H), 2.63 (d, J=13.8 Hz, 1H), 2.56-2.44 (m, 2H), 1.77 (s, 1H), 1.63-1.47 (m, 2H), 1.43-1.29 (m, 3H), 0.93 (d, J=6.8 Hz, 3H), 0.70 (d, J=5.4, 6H), 0.64 (d, J=5.2, 6H).

$^{13}$C NMR (100 MHz, CDCl$_3$) δ 173.2, 171.1, 170.5, 170.4, 169.6, 165.2, 148.8, 148.4, 137.6, 134.6, 134.5, 129.6, 128.9, 128.4, 127.1, 126.6, 122.2, 61.0, 54.8, 54.0, 52.9, 52.3, 52.2, 45.3, 39.8, 37.5, 37.2, 36.2, 35.3, 30.9, 29.7, 29.3, 24.9, 22.7, 21.7, 21.3, 15.7, 1.07.

Product 5

HRMS: Calcd for $C_{40}H_{49}N_6O_7$ [M+H$^+$]:725.3657; found: 725.3656.

$^1$H NMR (400 MHz, CDCl$_3$) δ 8.63 (d, J=4.4 Hz, 1H), 8.59 (d, J=8.2 Hz, 1H), 7.70 (t, J=7.2 Hz, 1H), 7.63 (d, J=7.6 Hz, 1H), 7.49-7.44 (m, 1H), 7.21 (d, J=4.6 Hz, 3H), 7.00 (d, J=7.4 Hz, 2H), 6.92 (s, 3H), 6.80 (d, J=6.4 Hz, 1H), 6.73 (d, J=8.6 Hz, 1H), 4.96-4.85 (m, 2H), 4.12 (t J=8.8 Hz, 1H), 4.05-3.98 (m, 1H), 3.82 (s, 3H), 3.68 (d, J=7.2 Hz, 1H), 3.65-3.57 (m, 2H), 3.41-3.30 (m, 2H), 3.21 (dd, J=14.0, 3.4 Hz, 1H), 3.05-2.99 (m, 1H), 2.95 (d, J=16.4 Hz, 11H), 2.77-2.67 (m, 1H), 2.47 (dd, J=11.4, 6.4 Hz, 1H), 2.30 (dd, J=14.4, 11.6 Hz, 1H), 1.99-1.76 (m, 4H), 1.68-1.59 (m, 1H), 1.41 (d, J=6.4 Hz, 4H), 0.79 (d, J=5.2 Hz, 3H), 0.72 (d, J=5.4 Hz, 3H).

$^{13}$C NMR (100 MHz, CDCl$_3$) δ 172.7, 171.5, 171.1, 170.6, 170.5, 165.7, 148.7, 148.6, 138.3, 137.6, 137.5, 134.9, 130.3, 129.0, 128.4, 126.9, 126.5, 122.4, 60.4, 55.0, 53.6, 53.2, 52.6, 49.0, 46.0, 39.9, 36.4, 34.7, 33.2, 30.7, 30.6, 24.9, 22.8, 21.9, 21.2.

Product 6a

HRMS: Calcd for $C_{42}H_{53}N_6O_7$ [M+H$^+$]:753.3970; found: 753.3975.

$^1$H NMR (400 MHz, CDCl$_3$) δ 8.73 (d, J=8.0 Hz, 1H), 8.66 (d, J=4.2 Hz, 1H), 7.86 (d, J=7.8 Hz, 1H), 7.75 (t, J=7.6 Hz, 1H), 7.64 (d, J=9.2 Hz, 1H), 7.51-7.45 (m, 1H), 7.22-7.14 (m, 6H), 7.05-6.97 (m, 4H), 6.69 (d, J=5.0 Hz, 1H), 5.04 (t, J=8.8 Hz, 1H), 4.81 (d, J=5.8 Hz, 1H), 4.46 (t, J=9.2 Hz, 1H), 4.19 (d, J=7.4 Hz, 1H), 4.13-4.03 (m, 1H), 3.73 (s, 3H), 3.62 (t, J=15.0 Hz, 2H), 3.47-3.38 (m, 1H), 3.26-3.12 (m, 3H), 2.89-2.80 (m, 1H), 2.35 (dd, J=12.0, 5.8 Hz, 1H), 2.30-2.22 (m, 1H), 1.96-1.84 (m, 1H), 1.83-1.73 (m, 2H), 1.37 (d, J=7.2 Hz, 3H), 1.25 (s, 2H), 0.88 (d, J=7.2 Hz, 3H), 0.79 (d, J=5.8 Hz, 3H), 0.70 (d, J=5.8 Hz, 3H).

$^{13}$C NMR (100 MHz, CDCl$_3$) δ 172.4, 172.0, 171.8, 171.6, 171.1, 165.5, 148.8, 148.6, 141.8, 138.1, 137 6, 128.9, 128.8, 128.7, 128.3, 128.1, 127.0, 126.9, 126.4, 122.5, 61.1, 55.1, 54.4, 53.4, 53.0, 52.4, 46.4, 43.4, 40.2, 39.7, 37.2, 36.8, 31.0, 24.9, 22.6, 22.0, 21.5, 20.7, 11.3.

Product 6b

HRMS: Calcd for $C_{42}H_{53}N_6O_7$ [M+H$^-$]:753.3970; found: 753.3974.

The product 6b should be a conformational isomer, which has different ratios in different deuterated solvents.

$^1$H NMR (400 MHz, CDCl3, ratio of isomer=2.5:1) δ 8.83 (d, J=8.6 Hz, 1H), 8.62 (dd, J=11.4, 4.4 Hz, 2H), 8.12 (d, J=7.6 Hz, 1H), 7.88 (d, J=7.8 Hz, 1H), 7.72 (t, J=7.0 Hz, 1H), 7.53-7.43 (m, 3H), 7.30 (d, J=7.6 Hz, 2H), 7.18 (t, J=5.2 Hz, 5H), 7.08 (t, J=8.8 Hz, 2H), 6.97 (d, J=6.4 Hz, 3H), 6.23 (d, J=4.4 Hz, 1H), 5.35 (t, J=5.2 Hz, 1H), 5.04-4.96 (m, 1H), 4.92 (td, J=8.0, 3.6 Hz, 1H), 4.51 (d, J=8.4 Hz, 1H), 4.03-3.97 (m, 1H), 3.79 (s, 3H), 3.77 (s, 1H), 3.60 (s, 1H), 3.53 (dd, J=11.8, 6.4 Hz, 3H), 3.46 (d, J=7.8 Hz, 1H), 3.24 (dd, J=19.6, 10.6 Hz, 2H), 3.16 (s, 1H), 3.12-3.04 (m, 1H), 3.00 (d, J=14.6 Hz, 2H), 2.36-2.26 (m, 1H), 2.22 (t, J=7.6 Hz, 1H), 2.10 (t, J=14.0 Hz, 2H), 2.02 (s, 1H), 1.89 (d, J=7.8 Hz, 3H), 1.79-1.70 (m, 2H), 1.63 (s, 7H), 1.18 (t, J=7.2 Hz, 5H), 0.89 (t, J=11.2 Hz, 5H), 0.82 (d, J=5.8 Hz, 4H).

$^1$H NMR (400 MHz, Acetone, ratio of isomer=1.3:1) δ 8.77 (d, J=9.4 Hz, 1H), 8.71 (dd, J=9.8, 4.7 Hz, 2H), 8.16 (d, J=7.8 Hz, 1H), 8.06 (t, J=8.6 Hz, 1H), 8.00 (d, J=7.8 Hz, 1H), 7.95 (dt, J=7.8, 3.8 Hz, 1H), 7.64 (d, J=11.2, 6.4 Hz, 2H), 7.50-7.46 (m, 1H), 7.39 (d, J=8.8 Hz, 1H), 7.33 (d, J=7.2 Hz, 2H), 7.31-7.26 (m, 3H), 7.23 (d, J=6.8 Hz, 4H), 7.21-7.14 (m, 1 OH), 7.13 (s, 1H), 7.12-7.07 (m, 2H), 6.99 (d, J=7.6 Hz, 1H), 5.35 (t, J=4.8 Hz, 1H), 4.83 (d, J=10.8 Hz, 1H), 4.78 (d, J=11.4 Hz, 2H), 4.73 (d, J=9.4 Hz, 2H), 4.66 (d, J=4.2 Hz, 1H), 4.15-4.06 (m, 1H), 3.97 (dt, J=10.2, 6.2 Hz, 2H), 3.75 (s, 1H), 3.72 (s, 3H), 3.71 (s, 2H), 3.63 (s, 1H), 3.57-3.50 (m, 2H), 3.50-3.42 (m, 2H), 3.23 (dd, J=19.6, 10.8 Hz, 2H), 3.16 (d, J=4.2 Hz, 2H), 3.13-3.02 (m, 4H), 2.93 (s, 3H), 2.82 (s, 5H), 2.41-2.29 (m, 1H), 2.14 (t, J=7.4 Hz, 1H), 1.85 (d, J=5.8 Hz, 4H), 1.72-1.50 (m, 5H), 1.48-1.39 (m, 4H), 1.12 (t, J=7.4 Hz, 4H), 1.06-0.97 (m, 4H), 0.88 (t, J=6.6 Hz, 4H), 0.84 (d, J=6.6 Hz, 3H), 0.78 (d, J=2.2 Hz, 3H), 0.76 (d, J=2.4 Hz, 3H), 0.71 (d, J=6.4 Hz, 3H).

Product 7

HRMS: Calcd for $C_{37}H_{49}N_6O_7$ [M+H$^-$]: 689.3657, found: 689.3661.

$^1$H NMR (400 MHz, CDCl$_3$) δ 8.71 (d, J=8.3 Hz, 1H), 8.57 (d, J=4.6 Hz, 1H), 8.12 (d, J=7.8 Hz, 1H), 7.82 (t, J=7.8 Hz, 1H), 7.42 (dd, J=7.4, 4.8 Hz, 1H), 7.28 (d, J=7.8 Hz, 1H), 7.18 (d, J=5.8 Hz, 2H), 7.09 (s, 1H), 7.07-7.00 (m, 3H), 6.39 (d, J=7.8 Hz, 1H), 4.74-4.67 (m, 1H), 4.53 (t, J=8.5 Hz, 1H), 4.46 (dd, J=8.2, 2.8 Hz, 1H), 4.42-4.33 (m, 2H), 4.10-4.05 (m, 1H), 3.79 (s, 3H), 3.70-3.64 (m, 1H), 3.47 (dd, J=17.2, 3.8 Hz, 1H), 3.24 (dd, J=13.6, 2.6 Hz, 1H), 3.04 (dd, J=13.6, 10.2 Hz, 1H), 2.86 (dd, J=13.8, 6.6 Hz, 1H), 2.60 (dd, J=13.8, 9.2 Hz, 1H), 2.32-2.21 (m, 1H), 2.20-2.14 (m, 3H), 2.05-1.99 (m, 1H), 1.76-1.56 (m, 9H), 1.44-1.33 (m, 1H), 1.18 (d, J=14.2 Hz, 2H), 1.09 (dd, J=21.0, 8.6 Hz, 3H), 0.99 (t, J=7.4 Hz, 3H).

$^{13}$C NMR (100 MHz, CDCl$_3$) δ 172.5, 171.7, 170.8, 170.5, 169.3, 164.1, 149.6, 148.4, 140.3, 137.3, 131.2, 129.2, 127.5, 127.2, 126.4, 122.2, 100.4, 60.9, 56.0, 54.1, 53.8, 52.6, 48.2, 45.0, 42.7, 40.3, 36.6, 36.3, 29.7, 29.5, 29.1, 26.2, 25.8, 25.7, 24.8, 22.7, 12.6.

Product 8

Product 8 is a mixture of diastereomers in a ratio of 2:1.

HRMS: Calcd for $C_{42}H_{53}N_6O_8$ [M+H$^+$]769.3919; found: 769.3922.

$^1$H NMR (400 MHz, CDCl$_3$) δ 9.16 (d, J=9.4 Hz, 1H), 8.69-8.52 (m, 2H), 8.18 (d, J=7.8 Hz, 1H), 7.88 (t, J=7.8 Hz, 11H), 7.82 (d, J=7.8 Hz, 11H), 7.71 (t, J=7.6 Hz, 11H), 7.57-7.51 (m, 1H), 7.50-7.41 (m, 2H), 7.24 (d, J=7.4 Hz, 2H), 7.21-7.16 (m, 3H), 7.13 (d, J=7.6 Hz, 3H), 7.11-7.05 (m, 2H), 6.95 (d, J=8.2 Hz, 1H), 6.84 (d, J=7.4 Hz, 11H), 6.79 (d, J=8.4 Hz, 2H), 6.72 (t, J=6.8 Hz, 2H), 6.56 (d, J=8.2 Hz, 1H), 5.12 (d, J=9.4 Hz, 1H), 4.87 (ddd, J=17.4, 8.0, 4.4 Hz, 2H), 4.73-4.52 (m, 2H), 4.48 (d, J=7.4 Hz, 1H), 4.29 (dd, J=15.4, 9.4 Hz, 2H), 4.15 (dd, J=13.8, 7.0 Hz, 1H), 3.80 (s, 3H), 3.73 (s, 3H), 3.70 (s, 3H), 3.68 (s, 1H), 3.53-3.45 (m, 1H), 3.30 (ddd, J=20.4, 14.4, 5.4 Hz, 1H), 3.18 (dd, J=14.0, 3.6 Hz, 1H), 3.09 (d, J=2.8 Hz, 1H), 2.99 (d, J=4.8 Hz, 1H), 2.97-2.94 (m, 1H), 2.92 (d, J=8.2 Hz, 1H), 2.87 (dd, J=8.4, 5.8 Hz, 1H), 2.80 (dd, J=15.8, 7.6 Hz, 1H), 2.74 (s, 1H), 2.62 (s, 1H), 2.43 (dd, J=11.0, 6.4 Hz, 1H), 2.21 (d, J=8.8 Hz, 1H), 2.16 (d, J=2.6 Hz, 1H), 2.01-1.88 (m, 4H), 1.87-1.77 (m, 1H), 1.74-1.62 (m, 1H), 1.59-1.45 (m, 3H), 1.41-1.29 (m, 3H), 1.08-0.99 (m, 6H), 0.91-0.78 (m, 10H), 0.74 (d, J=6.2 Hz, 1H).

Product 9

HRMS: Calcd for $C_{31}H_{39}N_6O_7$ [M+H$^-$]: 607.2875; found: 607.2878.

$^1$H NMR (600 MHZ, CDCl$_3$) δ 8.92 (d, J=7.8 Hz, 1H), 8.66 (d, J=4.6 Hz, 1H), 8.06 (d, J=7.8 Hz, 1H), 7.94 (s, 1H), 7.90 (d, J=7.8 Hz, 1H), 7.87 (s, 1H), 7.55-7.50 (m, 1H), 6.99 (d, J=7.8 Hz, 2H), 6.94 (d, J=7.8 Hz, 2H), 6.75 (d, J=6.6 Hz, 1H), 4.88 (d, J=3.4 Hz, 1H), 4.26-4.20 (m, 2H), 4.05 (dd, J=15.6, 5.4 Hz, 1H), 3.90 (d, J=6.6 Hz, 1H), 3.87 (s, 2H), 3.79 (s, 3H), 3.65 (s, 1H), 3.62 (d, J=6.0 Hz, 1H), 3.36 (dd, J=14.0, 5.6 Hz, 1H), 3.15 (dd, J=14.0, 3.2 Hz, 1H), 2.86 (d, J=13.8 Hz, 1H), 2.53 (d, J=13.8 Hz, 1H), 2.45 (d, J=5.8 Hz, 1H), 2.22 (t, J=12.2 Hz, 1H), 2.00 (s, 1H), 1.89 (s, 1H), 1.72 (s, 1H), 1.42 (s, 3H), 1.03 (s, 3H).

Product 10

HRMS: Calcd for $C_{28}H_{34}N_5O_6$ [M+H$^+$]: 536.2504; found: 536.2508.

$^1$H NMR (400 MHZ, CDCl$_3$) δ 8.61 (d, J=4.6 Hz, 1H), 8.51 (d, J=8.8 Hz, 1H), 8.16 (d, J=7.8 Hz, 1H), 7.85 (td, J=7.8, 1.6 Hz, 1H), 7.49-7.42 (m, 1H), 7.13 (d, J=8.0 Hz, 2H), 6.87 (s, 2H), 6.67 (d, J=8.6 Hz, 1H), 6.52 (dd, J=8.6, 4.0 Hz, 1H), 4.97 (dd, J=7.2, 4.6 Hz, 1H), 4.75 (d, J=8.8 Hz, 1H), 4.44 (dd, J=17.4, 9.0 Hz, 1H), 3.86 (t, J=7.6 Hz, 1H), 3.75 (d, J=4.6 Hz, 3H), 3.71-3.63 (m, 2H), 3.40 (dd, J=17.4, 4.2 Hz, 1H), 3.22 (dd, J=13.4, 2.2 Hz, 1H), 3.02 (d, J=13.4, 5.6 Hz, 1H), 2.81 (dd, J=14.2, 3.8 Hz, 1H), 2.68 (dd, J=11.6, 5.0 Hz, 1H), 2.46-2.34 (m, 1H), 2.13 (dd, J=11.0, 4.8 Hz, 1H), 2.03 (dd, J=11.8, 5.2 Hz, 1H), 1.94-1.83 (m, 1H), 1.79 (dd, J=19.4, 8.2 Hz, 1H), 1.39 (d, J=7.0 Hz, 3H).

$^{13}$C NMR (100 MHz, CDCl$_3$) δ 172.0, 170.8, 170.2, 168.7, 164.4, 149.9, 148.2, 137.9, 137.4, 132.2, 130.3, 129.3, 128.0, 126.3, 122.5, 77.4, 77.1, 76.8, 61.2, 55.3, 53.0, 52.1, 48.0, 43.0, 39.2, 37.6, 37.1, 29.7, 25.8, 23.1.

Product 11

HRMS: Calcd for $C_{38}H_{47}N_6O_5$ [M+H$^+$]. 667.3602; found: 667.3607.

$^1$H NMR (400 MHZ, CDCl$_3$) δ 8.74 (d, J=8.4 Hz, 1H), 8.66 (d, J=4.4 Hz, 1H), 8.04 (d, J=8.4 Hz, 2H), 7.80 (td, J=7.8, 1.4 Hz, 1H), 7.50 (dd, J=7.4, 4.8 Hz, 1H), 7.28 (t, J=5.4 Hz, 3H), 7.24 (d, J=7.8 Hz, 1H), 7.19 (t, J=6.8 Hz, 2H), 7.14 (d, J=8.2 Hz, 1H), 7.09-7.00 (m, 2H), 6.40 (d, J=3.8 Hz, 1H), 5.23 (dd, J=15.8, 9.8 Hz, 1H), 5.19-5.11 (m, 1H), 4.75-4.69 (m, 1H), 3.99-3.87 (m, 2H), 3.79 (dd, J=14.8, 3.4 Hz, 1H), 3.60 (d, J=8.0 Hz, 1H), 3.57-3.46 (m, 2H), 2.99 (t, J=13.6 Hz, 2H), 2.73 (dd, J=13.8, 4.8 Hz, 1H), 2.47-2.37 (s, 1H), 2.09 (dd, J=12.6, 6.2 Hz, 1H), 1.92-1.86 (m, 1H), 1.84-1.72 (m, 1H), 1.70-1.57 (m, 2H), 1.34-1.28 (m, 3H), 0.84 (d, J=5.8 Hz, 3H), 0.80 (d, J=7.2 Hz, 3H), 0.74 (d, J=5.8 Hz, 3H).

$^{13}$C NMR (100 MHZ, CDCl$_3$) δ 172.9, 172.0, 171.9, 171.5, 148.8, 148.5, 138.6, 137.7, 136.5, 129.9, 129.0, 128.3, 128.2, 127.1, 126.8, 126.6, 126.4, 122.5, 61.2, 55.9, 52.7, 52.1, 46.6, 42.6, 40.4, 38.7, 37.5, 37.4, 36.3, 32.0, 25.0, 22.5, 22.1, 21.7, 14.9.

Product 12

HRMS: Calcd for $C_{50}H_{69}N_{10}O_{11}S$ [M+H$^+$]: 1017.4863; found: 1017.4863.

$^1$H NMR (400 MHZ, DMSO) δ 9.02 (d, J=8.8 Hz, 1H), 8.68 (d, J=4.6 Hz, 1H), 8.32 (d, J=5.4 Hz, 1H), 8.20 (d, J=4.4 Hz, 1H), 8.05-7.99 (m, 2H), 7.94 (t, J=5.4 Hz, 1H), 7.83 (d, J=7.6 Hz, 1H), 7.74 (d, J=7.4 Hz, 1H), 7.64 (dd, J=7.8, 3.6 Hz, 1H), 7.11 (t, J=7.6 Hz, 1H), 7.02 (s, 1H), 6.96 (t, J=6.8 Hz, 2H), 6.69 (s, 1H), 6.39 (s, 1H), 4.64-4.54 (m, 1H), 4.46 (t, J=8.2 Hz, 1H), 4.05 (t, J=7.0 Hz, 1H), 3.99-3.91 (m, 1H), 3.85 (dd, J=16.8, 7.2 Hz, 1H), 3.70 (s, 3H), 3.65 (d, J=5.4 Hz, 2H), 3.39 (dd, J=16.6, 4.2 Hz, 1H), 3.21-3.14 (m, 1H), 3.03 (s, 2H), 2.95 (s, 2H), 2.87 (dd, J=13.8, 9.4 Hz, 1H), 2.78 (d, J=10.8 Hz, 1H), 2.47 (s, 3H), 2.41 (s, 3H), 2.08-2.01 (m, 1H), 1.99 (m, 3H), 1.64 (m, 1H), 1.55 (s, 1H), 1.43 (m, 1H), 1.40 (s, 8H), 1.30 (m, 2H), 1.23 (m, 1H), 1.16 (dd, J=14.0, 6.6 Hz, 1H), 0.83 (m, 9H).

Product 13

HRMS: Calcd for $C_{49}H_{70}N_9O_{12}$ [M+H$^+$]: 976.5138; found: 976.5141.

$^1$H NMR (400 MHZ, CDCl$_3$) δ 8.59 (dd, J=14.0, 6.2 Hz, 2H), 7.96 (d, J=7.8 Hz, 1H), 7.91-7.78 (m, 1H), 7.67 (s, 1H), 7.60 (d, J=9.2 Hz, 1H), 7.52-7.45 (m, 1H), 7.23 (s, 1H), 7.14 (d, J=7.8 Hz, 2H), 7.06 (d, J=9.6 Hz, 1H), 7.00 (d, J=76 Hz, 2H), 5.06 (1, J=8.8 Hz, 1H), 4.93 (dd, J=15.2, 7.2 Hz, 1H), 4.72 (t, J=8.4 Hz, 1H), 4.59 (dd, J=13.2, 6.6 Hz, 1H), 4.55-4.42 (m, 2H), 4.02 (m, 2H), 3.90-3.82 (m, 1H), 3.77 (s, 3H), 3.72-3.68 (m, 1H), 3.65 (d, J=5.6 Hz, 1H), 3.55 (dd, J=16.8, 4.8 Hz, 1H), 3.05 (dd, J=24.8, 10.4 Hz, 2H), 2.92-2.84 (m, 1H), 2.73 (s, 3H), 2.45-2.38 (m, 1H), 2.31 (d, J=6.8 Hz, 1H), 2.22 (d, J=5.8 Hz, 2H), 2.04 (dd, J=12.8, 5.6 Hz, 2H), 1.83 (dd, J=12.4, 78 Hz, 1H), 1.75-1.69 (m, 3H), 1.59 (d, J=10.4 Hz, 1H), 1.49 (s, 9H), 1.44 (d, J=7.8 Hz, 3H), 1.26 (s, 2H), 0.85 (t, J=6.6 Hz, 6H), 0.78 (d, J=6.4 Hz, 3H).

Product 14

HRMS: Calcd for $C_{27}H_{35}N_4O_5$ [M+H$^+$]: 495.2602; found: 495.2602.

$^1$H NMR (400 MHZ, CDCl$_3$) δ 8.88 (d, J=9.2 Hz, 1H), 8.65 (d, J=4.4 Hz, 1H), 8.20 (d, J=7.8 Hz, 1H), 7.86 (t, J=7.6 Hz, 1H), 7.49-7.42 (m, 1H), 7.23 (d, J=7.6 Hz, 1H), 7.13 (d, J=7.4 Hz, 1H), 6.94 (d, J=7.6 Hz, 1H), 6.89 (s, 1H), 6.23 (d, J=8.6 Hz, 1H), 6.12 (d, J=10.0 Hz, 1H), 4.83-4.73 (m, 2H), 4.09 (d, J=10.0 Hz, 1H), 3.85 (s, 3H), 3.35 (dd, J=13.6, 4.8 Hz, 1H), 2.87-2.75 (m, 2H), 2.54 (dd, J=14.6, 3.4 Hz, 1H), 2.40 (d, J=3.6 Hz, 1H), 1.32 (d, J=7.0 Hz, 4H), 0.92 (s, 9H).

$^{13}$C NMR (100 MHZ, CDCl$_3$) δ 172.1, 170.7, 169.8, 164.8, 149.8, 148.5, 141.2, 137.3, 136.1, 129.6, 129.2, 127.5, 126.7, 126.4, 122.5, 60.9, 56.0, 52.5, 39.9, 38.2, 37.6, 33.8, 26.3, 21.3.

Product 15a

HRMS: Calcd for $C_{27}H_{34}N_5O_4$ [M+H$^+$]: 492.2605; found: 492.2608.

$^1$H NMR (400 MHZ, CDCl$_3$, diastereomer, d.r.=3:1) δ 8.70 (t, J=5.6 Hz, 1H), 8.65 (d, J=4.2 Hz, 2H), 8.53 (s, 1H), 8.26 (d, J=4.2 Hz, 1H), 8.19 (d, J=7.8 Hz, 1H), 8.04 (s, 1H), 7.97 (d, J=7.6 Hz, 1H), 7.89 (t, J=7.8 Hz, 1H), 7.72 (t, J=7.6 Hz, 1H), 7.57 (d, J=10.6 Hz, 1H), 7.55-7.49 (m, 1H), 7.37 (t, J=7.6 Hz, 1H), 7.34-7.29 (m, 1H), 7.14 (t, J=7.4 Hz, 3H), 7.05 (s, 1H), 6.79 (s, 1H), 6.48 (s, 1H), 6.35 (d, J=5.6 Hz, 1H), 5.03 (dd, J=10.2, 4.8 Hz, 1H), 4.64 (dd, J=17.4, 9.4 Hz, 1H), 4.16 (dd, J=16.0, 6.8 Hz, 1H), 4.06 (dd, J=10.6, 7.2 Hz, 2H), 3.90 (t, J=8.6 Hz, 1H), 3.82 (dd, J=13.0, 6.0 Hz, 1H), 3.74-3.69 (m, 2H), 3.67 (d, J=5.6 Hz, 1H), 3.59 (dd, J=20.4, 9.2 Hz, 1H), 3.55-3.48 (m, 1H), 3.46-3.29 (m, 3H), 3.18 (s, 1H), 3.06 (d, J=13.8 Hz, 1H), 2.93 (d, J=14.8 Hz, 1H), 2.62-2.45 (m, 2H), 2.35-2.20 (m, 2H), 2.14 (d, J=11.2 Hz, 1H), 1.98 (s, 1H), 1.85 (s, 1H), 1.77-1.58 (m, 2H), 1.43 (d, J=7.2 Hz, 3H), 1.32 (d, J=7.2 Hz, 1H), 1.28 (d, J=7.2 Hz, 1H), 0.90 (d, J=7.2 Hz, 3H).

Product 15b

HRMS: Calcd for $C_{27}H_{34}N_5O_4$ [M+H$^+$]: 492.2605; found: 492.2607.

$^1$H NMR (400 MHZ, CDCl$_3$) δ 8.70 (d, J=7.8 Hz, 1H), 8.66 (d, J=4.4 Hz, 1H), 8.19 (d, J=7.8 Hz, 1H), 7.89 (t, J=7.6 Hz, 1H), 7.67 (s, 1H), 7.54-7.48 (m, 1H), 7.39 (t, J=7.6 Hz, 1H), 7.13 (t, J=7.4 Hz, 2H), 6.91 (s, 1H), 6.76 (s, 1H), 4.36 (d, J=7.6 Hz, 1H), 4.00 (dd, J=15.8, 6.2 Hz, 1H), 3.74-3.57 (m, 3H), 3.56-3.46 (m, 3H), 3.10 (dd, J=13.4, 2.8 Hz, 1H), 3.07-2.96 (m, 1H), 2.77-2.66 (m, 1H), 2.40 (dd, J=16.4, 8.8 Hz, 2H), 2.09 (dd, J=13.4, 5.6 Hz, 2H), 1.92-1.81 (m, 2H), 1.69-1.58 (m, 2H), 1.55-1.45 (m, 1H), 1.17 (t, J=7.4 Hz, 3H).

$^{13}$C NMR (100 MHZ, CDCl$_3$) δ 170.3, 148.6, 137.5, 130.4, 129.7, 128.1, 126.3, 122.7, 60.0, 51.8, 46.6, 45.4, 38.1, 36.6, 33.6, 30.9, 21.8, 21.5, 12.6.

The product 16 is the two diastereomers separated, designated as 16-1 and 16-2.

Product 16-1

HRMS: Calcd for $C_{41}H_{49}N_6O_7$ [M+H$^+$]: 737.3657; found: 737.3661.

$^1$H NMR (400 MHZ, CDCl$_3$) δ 8.62 (d, J=4.8 Hz, 1H), 8.57 (d, J=5.2 Hz, 1H), 7.69-7.62 (m, 2H), 7.50 (d, J=7.6 Hz, 1H), 7.42 (t, J=6.4 Hz, 1H), 7.15 (d, J=7.6 Hz, 6H), 7.02 (d, J=3.2 Hz, 2H), 6.95 (d, J=7.6 Hz, 2H), 6.06 (d, J=7.4 Hz, 1H), 4.63 (dd, J=14.8, 7.6 Hz, 1H), 4.48 (dt, J=11.6, 5.8 Hz, 1H), 4.33 (t, J=8.0 Hz, 1H), 4.18 (d, J=7.2 Hz, 1H), 3.79-3.72 (m, 1H), 3.69 (s, 3H), 3.57 (dd, J=10.0, 5.4 Hz, 1H), 3.48-3.40 (m, 1H), 3.14 (dd, J=13.6, 4.0 Hz, 1H), 3.02 (dd, J=14.2, 6.2 Hz, 1H), 2.86 (dd, J=14.4, 8.0 Hz, 1H), 2.73 (dd, J=13.6, 8.0 Hz, 1H), 2.64-2.50 (m, 2H), 1.98 (dd, J=16.8, 9.4 Hz, 2H), 1.78-1.61 (m, 3H), 1.49 (s, 2H), 1.19 (dd, J=14.8, 8.6 Hz, 1H), 0.96 (dd, J=11.6, 5.8 Hz, 1H), 0.87 (d, J=5.6 Hz, 3H), 0.82 (d, J=5.2 Hz, 3H).

Product 16-2

HRMS: Calcd for $C_{41}H_{49}N_6O_7$ [M+H$^+$]: 737.3657; found: 737.3658.

$^1$H NMR (400 MHZ, CDCl$_3$) δ 8.75 (d, J=6.0 Hz, 1H), 8.66 (s, 1H), 7.96 (s, 1H), 7.84-7.71 (m, 3H), 7.48 (s, 1H), 7.32 (s, 1H), 7.22 (t, J=7.6 Hz, 4H), 7.16-7.10 (m, 2H), 7.07 (d, J=6.4 Hz, 1H), 6.45 (s, 1H), 6.24 (d, J=9.0 Hz, 1H), 5.01 (s, 1H), 4.91 (d, J=5.8 Hz, 1H), 3.96-3.85 (m, 2H), 3.79 (s, 3H), 3.65 (d, J=11.2 Hz, 1H), 3.42-3.13 (m, 5H), 2.72 (d, J=5.6 Hz, 1H), 2.41 (dd, J=15.2, 7.8 Hz, 1H), 2.23 (s, 1H), 1.84 (s, 1H), 1.77-1.62 (m, 3H), 1.51 (d, J=6.4 Hz, 4H), 1.37-1.28 (m, 2H), 1.15 (d, J=5.8 Hz, 1H), 0.84 (d, J=4.8 Hz, 3H), 0.74 (d, J=5.2 Hz, 3H).

Product 17

HRMS: Calcd for $C_{29}H_{35}N_5O_6$ [M+H$^+$]: 550.2660; found: 550.2662.

$^1$H NMR (400 MHZ, CDCl$_3$) δ 8 27 (d, J=4.6 Hz, 1H), 7.92 (d, J=7.8 Hz, 1H), 7.79 (d, J=8.2 Hz, 1H), 7.71 (t, J=7.8 Hz, 1H), 7.40-7.32 (m, 1H), 7.21 (d, J=8.8 Hz, 2H), 7.01 (s, 1H), 6.92 (s, 1H), 6.89-6.81 (m, 2H), 6.73 (d, J=6.2 Hz, 1H), 5.45 (d, J=7.6 Hz, 1H), 5.21 (s, 1H), 4.58 (dd, J=17.4, 8.4 Hz, 1H), 3.85 (d, J=4.0 Hz, 1H), 3.64 (s, 3H), 3.59 (s, 1H), 3.54 (d, J=4.0 Hz, 1H), 3.16 (dd, J=14.2, 5.2 Hz, 1H), 3.05 (d, J=12.2 Hz, 1H), 2.26 (dd, J=16.0, 8.4 Hz, 1H), 1.24 (d, J=7.6 Hz, 1H), 1.05 (s, 10H), 0.99 (d, J=6.4 Hz, 2H), 0.94 (s, 1H).

$^{13}$C NMR (100 MHz, CDCl$_3$) δ 171.4, 169.3, 164.2, 149.2, 147.9, 137.2, 136.9, 135.7, 133.0, 128.2, 127.0, 126.4, 122.4, 63.9, 53.2, 52.1, 50.6, 43.0, 32.6, 26.7, 21.4, 19.8, 4.8.

Product 18

HRMS: Calcd for $C_{31}H_{38}N_5O_6$ [M+H$^+$]: 576.2817; found: 576.2816.

$^1$H NMR (400 MHZ, CDCl$_3$) δ 8.62 (d, J=4.0 Hz, 1H), 8.46 (d, J=9.0 Hz, 1H), 8.18 (d, J=8.0 Hz, 1H), 7.86 (t, J=7.0 Hz, 1H), 7.49-7.41 (m, 1H), 7.18-7.12 (m, 2H), 6.94 (dd, J=28.4, 7.2 Hz, 2H), 6.82 (d, J=8.6 Hz, 1H), 6.10 (s, 1H), 5.06 (s, 1H), 4.67 (d, J=9.0 Hz, 1H), 4.62 (dd, J=17.8, 9.6 Hz, 1H), 3.86 (t, J=7.8 Hz, 1H), 3.74 (s, 3H), 3.72-3.63 (m, 2H), 3.47 (dd, J=17.6, 4.0 Hz, 1H), 3.28 (d, J=11.6 Hz, 1H), 3.05 (dd, J=13.2, 5.4 Hz, 1H), 2.40 (t, J=10.0 Hz, 1H), 2.19 (dd, J=21.4, 13.4 Hz, 3H), 2.04 (d, J=16.8 Hz, 3H), 1.92-1.84 (m, 3H), 1.79-1.69 (m, 2H), 1.47 (dd, J=23.6, 13.8 Hz, 2H).

$^{13}$C NMR (100 MHZ, CDCl$_3$) δ 172.1, 170.7, 170.3, 168.4, 164.3, 150.0, 148.2, 143.5, 137.3, 132.8, 132.2, 129.2, 128.4, 127.2, 126.3, 122.6, 61.8, 58.6, 56.3, 53.2, 52.2, 48.1, 46.8, 46.1, 42.9, 37.1, 36.2, 34.9, 29.8, 29.4, 26.8, 26.2, 25.9, 18.5.

The product 19 is the two diastereomers separated, designated as 19-1 and 19-2.

Product 19-1

HRMS: Calcd for $C_{30}H_{36}N_5O_6$ [M+H$^+$]: 562.2660; found: 562.2657.

$^1$H NMR (400 MHZ, CDCl$_3$) δ 9.21 (s, 1H), 8.59 (d, J=4.4 Hz, 1H), 8.24 (d, J=4.0 Hz, 1H), 8.08 (d, J=7.8 Hz, 1H), 7.82 (t, J=7.0 Hz, 1H), 7.46 (dd, J=6.8, 5.0 Hz, 1H), 7.15 (s, 2H), 7.01 (d, J=9.8 Hz, 3H), 4.84-4.71 (m, 1H), 4.27 (dd, J=14.6, 7.0 Hz, 1H), 4.13 (d, J=7.4 Hz, 1H), 3.76 (s, 3H), 3.62-3.53 (m, 2H), 3.46-3.35 (m, 3H), 2.95 (dd, J=10.4, 4.6 Hz, 1H), 2.73 (dd, J=14.2, 12.6 Hz, 1H), 2.61 (dd, J=11.2, 6.4 Hz, 1H), 2.51 (dd, J=14.4, 9.6 Hz, 1H), 2.44-2.33 (m, 1H), 2.14-2.01 (m, 2H), 1.94-1.82 (m, 2H), 1.80-1.60 (m, 3H), 1.58-1.44 (m, 1H).

$^{13}$C NMR (100 MHZ, CDCl$_3$) δ 172.2, 171.7, 170.5, 169.8, 164.4, 148.5, 148.2, 142.3, 137.4, 135.2, 130.4, 127.1, 126.6, 125.6, 122.7, 61.1, 52.8, 52.4, $2.1, 49.3, 46.5, 45.3, 45.2, 36.5, 31.0, 30.6, 26.9, 24.5, 22.1.

Product 19-2

HRMS: Calcd for $C_{30}H_{36}N_5O_6$ [M+H$^+$]: 562.2660; found: 562.2659.

$^1$H NMR (400 MHZ, CDCl$_3$) δ 8.65 (d, J=8.8 Hz, 1H), 8.61 (d, J=4.4 Hz, 1H), 8.17 (d, J=7.8 Hz, 1H), 7.85 (t, J=7.2 Hz, 1H), 7.51-7.43 (m, 1H), 7.15 (d, J=7.8 Hz, 2H), 7.00 (s, 1H), 6.91 (s, 2H), 6.54 (d, J=8.4 Hz, 1H), 6.26 (s, 1H), 5.04 (d, J=9.0 Hz, 1H), 4.98 (s, 1H), 4.50 (dd, J=17.4, 8.8 Hz, 1H), 4.22 (dd, J=14.0, 7.0 Hz, 1H), 4.14 (s, 1H), 4.06-3.94 (m, 1H), 3.79 (s, 3H), 3.70 (dd, J=12.2, 6.6 Hz, 2H), 3.46 (dd, J=17.4, 3.8 Hz, 1H), 3.23 (d, J=11.4 Hz, 1H), 3.07 (dd, J=13.4, 5.6 Hz, 1H), 2.81-2.70 (m, 1H), 2.46 (dd, J=18.8, 10.8 Hz, 1H), 2.21-2.11 (m, 2H), 2.04 (d, J=7.6 Hz, 2H), 1.90 (dd, J=16.6, 6.2 Hz, 2H), 1.79-1.67 (m, 3H).

$^{13}$C NMR (100 MHz, CDCl$_3$) δ 172.2, 171.0, 170.2, 168.5, 164.3, 149.9, 148.3, 141.8, 137.4, 132.7, 126.3, 122.5, 60.7, 53.2, 51.3, 50.4, 47.8, 43.1, 37.1, 35.2, 32.0, 29.6, 25.5, 22.3.

Product 20

HRMS: Calcd for $C_{26}H_{31}N_5O_4$ [M+H$^+$]: 478.2449; found: 478.2448.

$^1$H NMR (400 MHZ, Acetone) δ 8.79 (d, J=8.8 Hz, 1H), 8.70 (d, J=4.4 Hz, 1H), 8.40 (d, J=4.4 Hz, 2H), 8.27 (s, 2H), 8.18 (d, J=7.7 Hz, 1H), 8.05 (dd, J=13.6, 6.0 Hz, 3H), 7.96 (d, J=7.6 Hz, 2H), 7.89 (t, J=7.2 Hz, 3H), 7.67-7.61 (m, 1H), 7.60-7.51 (m, 1H), 7.50-7.43 (m, 1H), 7.35-7.26 (m, 2H), 7.16 (s, 3H), 7.00 (d, J=6.8 Hz, 1H), 6.91 (d, J=7.6 Hz, 3H), 6.77 (d, J=7.2 Hz, 2H), 6.65 (t, J=7.6 Hz, 2H), 4.93-4.86 (m, 2H), 4.38 (d, J=8.4 Hz, 1H), 4.32 (dd, J=16.5, 8.8 Hz, 3H), 4.24-4.17 (m, 1H), 4.01 (dd, J=13.2, 6.6 Hz, 4H), 3.81-3.72 (m, 2H), 3.72-3.66 (m, 2H), 3.61-3.51 (m, 2H), 3.50-3.47 (m, 2H), 3.45-3.42 (m, 1H), 3.38 (dd, J=9.2, 4.9 Hz, 2H), 3.17-3.08 (m, 2H), 3.02-2.94 (m, 1H), 2.94-2.84 (m, 4H), 2.83 (s, 5H), 2.80 (s, 4H), 2.76-2.70 (m, 1H), 2.51 (d, J=5.2 Hz, 1H), 2.47 (d, J=4.8 Hz, 1H), 2.45-2.41 (m, 2H), 2.39 (d, J=2.2 Hz, 1H), 2.36 (d, J=2.2 Hz, 1H), 2.33-2.27 (m, 2H), 2.25-2.19 (m, 2H), 2.16-2.09 (m, 2H), 2.01-1.94 (m, 4H), 1.78 (t, J=12.8 Hz, 2H), 1.56 (dd, J=17.2, 10.3 Hz, 1H), 1.36 (d, J=7.2 Hz, 3H), 1.21 (d, J=6.8 Hz, 7H).

Product 21

HRMS: Calcd for $C_{27}H_{33}N_4O_7$ [M+H$^+$]: 525.2344; found: 525.2347.

$^1$H NMR (400 MHZ, CDCl$_3$) δ 8.48 (d, J=8.8 Hz, 1H), 8.43 (s, 1H), 8.01 (d, J=7.4 Hz, 1H), 7.66 (t, J=7.6 Hz, 1H), 7.57 (d, J=6.8 Hz, 1H), 7.26-7.20 (m, 1H), 7.06 (d, J=1.8 Hz, 1H), 7.04 (s, 1H), 7.02 (s, 1H), 7.01-6.99 (m, 1H), 6.67 (d, J=9.0 Hz, 1H), 6.57 (d, J=8.6 Hz, 1H), 5.11 (s, 1H), 4.96 (d, J=11.0 Hz, 1H), 4.62 (d, J=9.0 Hz, 1H), 4.41 (s, 1H), 3.88 (t, J=10.0 Hz, 1H), 3.55 (s, 3H), 2.77 (d, J=12.8 Hz, 1H), 2.03 (dd, J=28.6, 16.0 Hz, 2H), 1.87 (d, J=6.4 Hz, 1H), 0.95 (d, J=5.6 Hz, 3H), 0.77 (dd, J=14.2, 6.0 Hz, 6H).

$^{13}$C NMR (100 MHZ, CDCl$_3$) δ 171.0, 164.7, 148.4, 141.4, 137.2, 133.9, 130.8, 129.9, 128.6, 127.3, 126.3, 122.3, 109.9, 77.3, 77.0, 76.7, 58.4, 56.6, 53.0, 50.8, 42.1, 37.6, 32.3, 19.1, 18.3, 18.2.

Product 22

HRMS: Calcd for C$_{34}$H$_{40}$N$_5$O$_6$ [M+H$^-$]: 614.2973; found: 614.2977.

$^1$H NMR (400 MHZ, CDCl$_3$) δ 8.78 (d, J=6.8 Hz, 1H), 8.69-8.51 (m, 3H), 8.09 (t, J=6.8 Hz, 2H), 7.91-7.79 (m, 4H), 7.76 (s, 1H), 7.61 (s, 1H), 7.49 (s, 2H), 7.47-7.41 (m, 2H), 7.38 (d, J=3.4 Hz, 2H), 7.19 (dd, J=19.0, 6.6 Hz, 6H), 7.11 (d, J=5.4 Hz, 4H), 6.72 (d, J=6.0 Hz, 1H), 6.47 (s, 1H), 6.15 (s, 1H), 6.06 (s, 1H), 4.70 (d, J=5.2 Hz, 1H), 4.64 (s, 3H), 4.50 (s, 1H), 4.36 (s, 1H), 3.72 (s, 3H), 3.71 (s, 2H), 3.41 (d, J=9.2 Hz, 1H), 3.17 (d, J=13.8 Hz, 4H), 2.96 (ddd, J=21.6, 20.8, 14.0 Hz, 4H), 2.82 (dd, J=13.6, 7.6 Hz, 1H), 2.64 (d, J=11.4 Hz, 3H), 2.42 (s, 1H), 2.02 (s, 3H), 1.88 (s, 1H), 1.45 (d, J=12.8 Hz, 8H), 1.04 (d, J=6.2 Hz, 3H), 0.94 (d, J=5.6 Hz, 2H).

Product 23

HRMS: Calcd for C$_{44}$H$_{50}$N$_5$O$_9$ [M+H$^+$]: 792.3603; found: 792.3604.

$^1$H NMR (400 MHz, DMSO) δ 8.73-8.66 (m, 2H), 8.57 (L, J=9.6 Hz, 2H), 8.09-8.01 (m, 2H), 7.68-7.62 (m, 1H), 7.42-7.25 (m, 10H), 7.19 (t, J=7.6 Hz, 2H), 7.10 (d, J=7.6 Hz, 1H), 7.03 (d, J=7.6 Hz, 1H), 6.87 (s, 1H), 5.35 (d, J=13.6 Hz, 1H), 5.20-5.11 (m, 2H), 4.97 (s, 2H), 4.88 (t, J=10.9 Hz, 2H), 4.67-4.58 (m, 2H), 2.97-2.86 (m, 2H), 2.74 (d, J=10.4 Hz, 1H), 2.61-2.53 (m, 2H), 2.29-2.17 (m, 1H), 2.13 (s, 1H), 2.11-1.94 (m, 1H), 1.84-1.73 (m, 1H), 1.62 (d, J=7.6 Hz, 1H), 1.48 (dd, J=13.6, 7.2 Hz, 1H), 1.35-1.26 (m, 4H), 0.85 (d, J=5.6 Hz, 3H).

$^{13}$C NMR (101 MHZ, DMSO) δ 172.0, 171.8, 171.5, 170.6, 163.3, 156.1, 149.2, 148.7, 140.9, 138.2, 137.3, 136.6, 135.9, 128.7, 128.5, 128.4, 128.2, 128.0, 127.8, 127.0, 126.0, 124.2, 121.9, 66.3, 65.1, 64 6, 55.8, 51.8, 50.0, 41, 1, 36.4, 33.2, 31.4, 29.4, 29.2, 29.1, 28.8, 26.1, 22.5, 16.7.

Product 25

HRMS: Calcd for C$_{31}$H$_{42}$N$_7$O$_5$ [M+H$^+$]: 592.3242; found: 592.3242.

$^1$H NMR 600 MHZ, CD$_3$COOD) δ 8.62 (s, 1H), 8.58 (d, J=4.4 Hz, 1H), 8.06 (d, J=8.0 Hz, 1H), 7.98 (d, J=7.2 Hz, 1H), 7.87 (dd, J=15.0, 7.4 Hz, 1H), 7.50 (s, 1H), 7.16 (d, J=7.8 Hz, 1H), 7.11 (d, J=7.2 Hz, 1H), 6.99 (s, 2H), 6.83 (d, J=7.6 Hz, 1H), 4.96 (d, J=9.2 Hz, 1H), 4.80 (d, J=9.2 Hz, 1H), 4.28 (s, 1H), 4.19 (s, 1H), 4.10 (s, 1H), 3.63 (d, J=24.6 Hz, 1H), 3.59-3.52 (m, 1H), 3.48 (s, 1H), 3.29 (d, J=12.0 Hz, 1H), 3.04 (d, J=10.2 Hz, 1H), 2.94 (s, 3H), 2.72 (t, J=12.4 Hz, 2H), 2.63-2.56 (m, 1H), 2.50-2.38 (m, 1H), 2.27-2.17 (m, 1H), 2.08 (dd, J=18.8, 4.8 Hz, 1H), 1.62 (s, 4H), 1.48 (s, 3H), 1.27 (d, J=6.4 Hz, 3H), 1.09 (d, J=8.0 Hz, 3H).

Product 26

HRMS: Calcd for C$_{30}$H$_{38}$N$_7$O$_6$ [M+H$^+$]: 592.2878; found: 592.2879.

$^1$H NMR (600 MHZ, CD$_3$OD) δ 8.78 (d, J=4.0 Hz, 1H), 8.74 (d, J=4.0 Hz, 1H), 8.15 (s, 1H), 8.14 (s, 1H), 8.02 (d, J=4.0 Hz, 2H), 7.64 (s, 2H), 7.31 (d, J=7.6 Hz, 1H), 7.24 (d, J=6.6 Hz, 2H), 7.15 (d, J=7.6 Hz, 1H), 7.11 (d, J=7.8 Hz, 1H), 7.06 (d, J=7.0 Hz, 2H), 6.97 (d, J=7.2 Hz, 2H), 4.84 (s, 1H), 4.76-4.70 (m, 1H), 4.37 (s, 1H), 4.23-4.18 (m, 1H), 4.05 (d, J=6.2 Hz, 1H), 3.96 (s, 1H), 3.76 (d, J=17.2, 7.2 Hz, 2H), 3.57 (dd, J=19.2, 11.4 Hz, 2H), 3.41-3.35 (m, 2H), 3.20-3.15 (m, 2H), 3.08 (dd, J=11.6, 6.2 Hz, 2H), 2.85 (d, J=17.6 Hz, 2H), 2.79 (t, J=13.6 Hz, 1H), 2.71 (s, 2H), 2.60 (s, 3H), 2.35-2.15 (m, 11H), 2.10-2.00 (m, 3H), 1.93 (d, J=5.6 Hz, 2H), 1.41 (d, J=6.8 Hz, 3H), 1.21 (d, J=7.2 Hz, 3H).

Product 27

HRMS: Calcd for C$_{31}$H$_{42}$N$_9$O$_5$ [M+H$^+$]: 565.2769; found: 565.2772.

$^1$H NMR (400 MHz, DMSO) δ 8.75 (d, J=4.4 Hz, 1H), 8.67 (d, J=8.8 Hz, 1H), 8.07 (t, J=9.4 Hz, 2H), 7.67 (s, 1H), 7.46 (d, J=9.6 Hz, 1H), 7.30 (s, 1H), 7.25 (s, 1H), 6.98 (s, 4H), 6.29 (s, 1H), 5.13 (d, J=4.0 Hz, 1H), 4.77 (d, J=8.8 Hz, 1H), 4.41-4.21 (m, 2H), 4.09 (s, 2H), 3.65 (s, 2H), 3.00 (d, J=9.6 Hz, 2H), 2.89 (s, 1H), 2.59 (d, J=10.6 Hz, 1H), 2.34 (d, J=9.6 Hz, 2H), 2.00 (s, 4H), 1.87 (s, 1H), 1.78 (s, 1H), 1.33 (d, J=6.8 Hz, 3H), 0.85 (d, J=4.8 Hz, 3H).

Product 28

HRMS: Calcd for C$_{31}$H$_{42}$N$_9$O$_5$ [M+H$^+$]: 620.3303; found: 620.3307.

$^1$H NMR (400 MHZ, CD$_3$OD) δ 8.74 (d, J=7.6 Hz, 2H), 8.54 (s, 1H), 8.12 (d, J=7.6 Hz, 1H), 8.06 (d, J=7.6 Hz, 1H), 8.02-7.96 (m, 2H), 7.66-7.57 (m, 2H), 7.30 (d, J=7.6 Hz, 1H), 7.22-7.02 (m, 6H), 6.95 (d, J=7.6 Hz, 1H), 4.82 (s, 1H), 4.72 (d, J=4.8 Hz, 1H), 4.34 (t, J=7.2 Hz, 1H), 4.25 (s, 1H), 4.05 (d, J=6.8 Hz, 1H), 3.92 (s, 1H), 3.74 (s, 2H), 3.61-3.53 (m, 1H), 3.40-3.33 (m, 1H), 3.24-3.08 (m, 7H), 2.99-2.90 (m, 1H), 2.84 (d, J=14.0 Hz, 1H), 2.80-2.65 (m, 3H), 2.60-2.52 (m, 3H), 2.10-1.99 (m, 4H), 1.98-1.89 (m, 4H), 1.86 (d, J=5.6 Hz, 2H), 1.61-1.47 (m, 5H), 1.39 (d, J=6.4 Hz, 3H), 1.20 (d, J=7.2 Hz, 3H).

Product 29

HRMS: Calcd for C$_{34}$H$_{45}$N$_8$O$_7$ [M+H$^+$]: 677.3406; found: 677.3406.

$^1$H NMR (400 MHZ, DMSO) δ 8.97 (s, 1H), 8.77 (d, J=4.6 Hz, 1H), 8.03 (d, J=8.2 Hz, 1H), 7.98-7.91 (m, 2H), 7.69-7.64 (m, 1H), 7.59 (d, J=5.4 Hz, 1H), 7.44 (d, J=8.2 Hz, 1H), 7.40 (s, 1H), 7.30 (s, 1H), 7.26 (s, 1H), 7.14-7.07 (m, 1H), 7.04 (s, 1H), 7.01 (d, J=7.8 Hz, 1H), 6.91 (t, J=7.6 Hz, 1H), 6.83 (s, 1H), 6.71 (s, 1H), 4.21-4.12 (m, 1H), 3.95 (d, J=8.4 Hz, 1H), 3.77 (d, J=5.4 Hz, 1H), 3.37 (d, J=6.4 Hz, 1H), 2.96 (d, J=11.0 Hz, 3H), 2.62 (t, J=12.6 Hz, 1H), 2.41 (t, J=6.4 Hz, 2H), 2.34 (dd, J=14.8, 7.6 Hz, 1H), 2.01 (s, 3H), 1.88-1.75 (m, 2H), 1.35 (d, J=6.6 Hz, 1H), 1.07 (dd, J=13.8, 8.4 Hz, 1H), 0.95 (m, 1H), 0.88 (s, 9H).

Product 30

HRMS: Calcd for C$_{54}$H$_{80}$N$_{17}$O$_{13}$ [M+H$^+$]: 1174.6116; found: 1174.6118.

$^1$H NMR (600 MHZ, CD$_3$OD, 6:1 mixture of diastereoisomers) δ 8.68-8.65 (m, 1H), 8.51 (s, 2H), 8.14-8.09 (m, 1H), 8.02-7.98 (m, 1H), 7.61 (dd, J=7.2, 5.2 Hz, 1H), 7.19 (s, 3H), 7.17 (d, J=4.8 Hz, 1H), 5.35 (dd, J=12.4, 7.6 Hz, 1H), 5.01 (d, J=4.8 Hz, 1H), 4.62 (dd, J=8.4, 4.0 Hz, 1H), 4.55-4.52 (m, 1H), 4.47-4.39 (m, 3H), 4.38-4.31 (m, 2H), 4.10 (t, J=13.2 Hz, 1H), 4.03-3.90 (m, 4H), 3.86-3.82 (m, 2H), 3.78-3.71 (m, 2H), 3.70-3.58 (m, 3H), 3.35 (s, 2H), 3.24-3.19 (m, 2H), 3.19-3.11 (m, 2H), 3.02-2.94 (m, 2H), 2.94-2.89 (m, 3H), 2.40-2.28 (m, 5H), 2.21 (m, 4H), 2.16-2.07 (m, 3H), 2.02 (m, 5H), 1.96-1.82 (m, 5H), 1.77 (dd, J=13.6, 5.6 Hz, 1H), 1.70 (dd, J=14.8, 8.0 Hz, 4H), 1.67-1.59 (m, 3H), 1.42 (dd, J=27.6, 4.4 Hz, 2H), 1.36-1.31 (m, 2H), 0.91 (d, J=7.2 Hz, 3H).

Product 31

HRMS: Calcd for C$_{27}$H$_{30}$N$_5$O$_6$ [M−H$^+$]: 520.2202; found: 520 2200.

$^1$H NMR (400 MHZ, MeOD) δ 8.79 (s, 1H), 8.11 (d, J=7.6 Hz, 1H), 8.01 (t, J=7.2 Hz, 1H), 7.67-7.58 (m, 1H), 7.25-7.04 (m, 3H), 6.77 (s, 1H), 4.78 (d, J=5.6 Hz, 2H), 4.28 (dd, J=17.2, 2.4 Hz, 1H), 4.17 (d, J=6.4 Hz, 1H), 3.72 (s, 2H), 3.49 (d, J=17.2 Hz, 1H), 3.35 (s, 3H), 3.25 (d, J=13.2

Hz, 1H), 3.03 (dd, J=13.2, 5.2 Hz, 1H), 2.78 (dd, J=23.6, 10.4 Hz, 2H), 2.46-2.34 (m, 1H), 2.21-2.16 (m, 2H), 2.06-1.92 (m, 2H), 1.91-1.82 (m, 1H), 1.36 (d, J=5.2 Hz, 3H).

Product 32

HRMS: Calcd for $C_{31}H_{44}N_9O_5$ [M+H$^+$]: 622.3460; found: 622.3458.

$^1$H NMR (400 MHZ, DMSO) δ 8.72 (d, J=4.4 Hz, 1H), 8.67-8.59 (m, 2H), 8.56 (d, J=8.0 Hz, 1H), 8.06 (q, J=7.6 Hz, 2H), 7.71-7.64 (m, 1H), 7.60 (d, J=8.4 Hz, 2H), 7.53 (s, 1H), 7.12 (1, J 7.6 Hz, 2H), 7.00 (s, 1H), 6.99-6.93 (m, 2H), 6.92 (s, 1H), 4.81 (d, J=9.2 Hz, 1H), 4.54 (t, J=6.4 Hz, 1H), 4.45 (dd, J=14.0, 7.2 Hz, 1H), 4.26-4.17 (m, 1H), 3.12 (d, J=6.4 Hz, 2H), 2.96 (d, J=8.8 Hz, 2H), 2.65 (d, J=12.0 Hz, 1H), 2.28 (m, 1H), 2.16-1.99 (m, 2H), 1.61 (s, 2H), 1.52-1.39 (m, 2H), 0.88 (s, 3H), 0.87 (s, 3H), 0.82 (d, J=6.4 Hz, 3H).

Product 33

HRMS: Calcd for $C_{37}H_{50}N_{11}O_9$ [M+H$^+$]: 792.3787; found: 792.3787.

$^1$H NMR (600 MHz, DMSO) δ 8.70 (dd, J=9.2, 7.8 Hz, 2H), 8.13 (s, 3H), 8.08 (d, J=7.8 Hz, 2H), 8.06-8.01 (m, 2H), 7.99 (d, J=7.8 Hz, 1H), 7.73 (d, J=8.4 Hz, 1H), 7.65 (dd, J=9.0, 3.0 Hz, 1H), 7.58 (s, 1H), 7.42 (s, 1H), 7.26 (s, 1H), 7.13 (d, J=7.8 Hz, 2H), 7.02 (d, J=7.8 Hz, 2H), 6.84 (s, 1H), 4.88 (d, J=10.8 Hz, 1H), 4.62 (dd, J=14.4, 7.2 Hz, 1H), 4.47-4.43 (m, 1H), 4.39 (td, J=9.6, 3.6 Hz, 1H), 4.08 (q, J=6.6 Hz, 1H), 3.93 (dd, J=17.4, 6.0 Hz, 1H), 3.15-3.07 (m, 4H), 2.99 (t, J=11.4 Hz, 2H), 2.77 (dd, J=14.4, 9.6 Hz, 1H), 2.58-2.53 (m, 1H), 2.34-2.25 (m, 2H), 2.13 (s, 2H), 1.94 (t, J=11.4 Hz, 1H), 1.88-1.82 (m, 4H), 1.69-1.67 (m, 1H), 1.60-1.58 (m, 3H), 1.49-1.45 (m, 1H), 0.89 (d, J=6.6 Hz, 3H).

Product 34

HRMS: Calcd for C58H93N4O11 [M+H+]: 1161.7143; found: 1161.7143. The product 34 is unseparated diastereomers in a ratio of 2:1.

Product 35

HRMS: Calcd for $C_{37}H_{41}N_4O_7$ [M+H$^+$]: 653.2970; found: 653.2969.

$^1$H NMR (400 MHZ, CDCl$_3$) δ 7.83-7.77 (m, 2H), 7.68-7.62 (m, 2H), 7.40 (ddd, J=24.4, 15.2, 7.2 Hz, 5H), 7.06 (d, J=6.8 Hz, 1H), 6.82 (d, J=7.2 Hz, 1H), 6.75 (d, J=6.0 Hz, 2H), 6.67 (d, J=8.4 Hz, 1H), 6.18 (dd, J=9.2, 3.6 Hz, 1H), 5.17 (d, J=8.0 Hz, 1H), 4.99 (dd, J=7.2, 4.8 Hz, 1H), 4.65 (dd, J=10.8, 6.4 Hz, 1H), 4.57 (dd, J=17.6, 9.2 Hz, 1H), 4.37 (dd, J=10.8, 6.0 Hz, 1H), 4.22 (dd, J=13.6, 7.2 Hz, 2H), 3.87 (t, J=7.6 Hz, 1H), 3.60 (s, 3H), 3.57-3.52 (m, 1H), 3.47 (dd, J=17.6, 4.0 Hz, 1H), 3.20 (dd, J=13.4, 2.2 Hz, 1H), 3.03 (dd, J=13.2, 5.6 Hz, 1H), 2.73 (dd, J=14.2, 4.0 Hz, 1H), 2.58-2.46 (m, 1H), 2.23-2.04 (m, 3H), 2.00-1.91 (m, 1H), 1.84 (dd, J=18.4, 7.6 Hz, 1H), 1.31 (d, J=7.6 Hz, 3H).

$^{13}$C NMR (100 MHz, CDCl$_3$) δ 172.0, 170.8, 170.2, 168.7, 164.4, 149.9, 148.2, 137.9, 137.4, 132.2, 130.3, 129.3, 128.0, 127.8, 126.3, 125.1, 124.8, 120.1, 77.4, 77.1, 76.8, 61.2, 55.3, 53.0, 52.1, 48.0, 43.0, 39.2, 37.6, 37.1, 29.7, 25.8, 23.1.

Product 36

HRMS: Calcd for $C_{40}H_{53}N_6O_8$ [M+H$^+$]: 745.3919; found: 745.3919.

$^1$H NMR (400 MHZ, CDCl$_3$) δ 9.13 (d, J=6.4 Hz, 1H), 8.13 (s, 1H), 7.34 (d, J=7.6 Hz, 2H), 7.28 (d, J=7.6 Hz, 1H), 7.25 (s, 1H), 7.20 (dd, J=11.6, 6.6 Hz, 2H), 6.93 (d, J=6.8 Hz, 2H), 6.85 (d, J=7.2 Hz, 3H), 6.63 (d, J=5.6 Hz, 2H), 4.88 (dd, J=13.8, 5.8 Hz, 1H), 4.75 (d, J=4.0 Hz, 1H), 4.32-4.23 (m, 1H), 4.11-4.04 (m, 2H), 3.99-3.88 (m, 2H), 3.75 (s, 3H), 3.60 (dd, J=22.0, 10.0 Hz 2H), 3.45 (dd, J=13.6, 4.8 Hz, 1H), 3.08 (dd, J=23.6, 9.2 Hz, 2H), 2.85 (d, J=14.0, 11.2 Hz, 1H), 2.77-2.62 (m, 3H), 2.59-2.45 (m, 4H), 1.82 (s, 1H), 1.68-1.60 (m, 2H), 1.38-1.19 (m, 4H), 0.92 (d, J=7.2 Hz, 3H), 0.79 (d, J=5.6 Hz, 3H), 0.69 (d, J=5.6 Hz, 3H).

$^{13}$C NMR (100 MHZ, CDCl$_3$) δ 180.0, 174.6, 173.0, 172.6, 170.7, 170.5, 169.1, 137.9, 134.8, 129.6, 129.3, 128.4, 126.8, 77.4, 77.1, 76.8, 61.3, 58.6, 54.8, 54.3, 53.9, 52.9, 52.4, 45.6, 40.0, 38.0, 37.8, 35.6, 35.1, 29.5, 25.3, 25.1, 22.8, 21.7, 16.1.

Product 37

$^1$H NMR (400 MHZ, CDCl$_3$) δ 8.66 (d, J=7.7 Hz, 1H), 8.59 (d, J=4.7 Hz, 1H), 7.66 (t, J=7.0 Hz, 1H), 7.49 (d, J=7.7 Hz, 1H), 7.47-7.38 (m, 1H), 7.25 (s, 1H), 7.21-7.12 (m, 5H), 7.06 (d, J=4.5 Hz, 1H), 6.96 (d, J=7.6 Hz, 2H), 6.71 (d, J=6.7 Hz, 1H), 6.59 (d, J=8.4 Hz, 1H), 5.47 (s, 1H), 5.24 (s, 1H), 4.97-4.85 (m, 2H), 4.51 (dd, J=14.7, 7.7 Hz, 1H), 4.06-3.97 (m, 1H), 3.68 (d, J=7.8 Hz, 1H), 3.66-3.58 (m, 1H), 3.46 (dd, J=15.2, 3.2 Hz, 1H), 3.34-3.22 (m, 3H), 3.04 (dd, J=15.9, 10.0 Hz, 3H), 2.38 (dd, J=12.1, 5.9 Hz, 1H), 2.00 (s, 1H), 1.86 (s, 2H), 1.80-1.66 (m, 2H), 1.59 (s, 2H), 1.35 (d, J=7.5 Hz, 2H), 1.33 (s, 1H), 0.85 (d, J=7.0 Hz, 1H), 0.72 (d, J=6.1 Hz, 3H), 0.67 (d, J=6.2 Hz, 3H).

Product 38

$^1$H NMR (400 MHZ, Acetone) δ 8.61-8.54 (m, 2H), 8.10-8.02 (m, 2H), 7.97 (td, J=7.6, 1.6 Hz, 1H), 7.85-7.78 (m, 1H), 7.61-7.57 (m, 1H), 7.57-7.54 (m, 1H), 7.50 (td, J=7.2, 1.6 Hz, 2H), 7.38 (dd, J=7.2, 1.6 Hz, 1H), 7.21 (s, 4H), 6.97 (d, J=7.2 Hz, 2H), 5.69-5.64 (m, 1H), 4.60-4.55 (m, 1H), 4.45-4.33 (m, 2H), 4.03 (d, J=8.4 Hz, 1H), 3.74 (s, 3H), 3.72-3.65 (m, 1H), 3.54-3.45 (m, 3H), 3.24 (dd, J=13.6, 5.2 Hz, 1H), 3.07-3.02 (m, 1H), 1.96-1.71 (m, 4H).

Product 39: HRMS: Calcd for $C_{27}H_{34}N_5O_7$ [M+H$^+$]: 540.2453; found: 540.2455.

Product 40: HRMS: Calcd for $C_{27}H_{33}N_6O_6$ [M+H$^+$]: 537.2456; found: 537.2459.

Product 41: HRMS: Calcd for $C_{27}H_{33}N_6O_8$ [M+H$^+$]: 581.2354; found: 581.2353.

Product 42: HRMS: Calcd for $C_{25}H_{34}N_5O_7$ [M+H$^+$]: 516.2453; found: 516.2457.

Product 43

$^1$H NMR (400 MHZ, CDCl$_3$) δ 8.70 (d, J=7.6 Hz, 1H), 8.62 (d, J=4.4 Hz, 1H), 7.63 (t, J=7.8 Hz, 1H), 7.44 (dd, J=12.8, 6.6 Hz, 2H), 7.37 (d, J=7.4 Hz, 1H), 7.25 (s, 2H), 7.22 (d, J=3.4 Hz, 2H), 7.02 (t, J=10.0 Hz, 4H), 6.83 (s, 1H), 6.72 (d, J=8.2 Hz, 1H), 6.22 (s, 1H), 5.55 (s, 1H), 4.90 (s, 1H), 4.78 (d, J=7.8 Hz, 1H), 4.08 (t, J=8.4 Hz, 1H), 3.94 (s, 1H), 3.88 (d, J=7.6 Hz, 1H), 3.64 (d, J=20.6, 9.8 Hz, 1H), 3.55 (d, J=13.2 Hz, 1H), 3.46 (d, J=13.4 Hz, 1H), 3.33 (t, J=10.0 Hz, 2H), 3.26-3.09 (m, 3H), 3.04 (dd, J=13.6, 5.8 Hz, 1H), 2.68 (dd, J=14.2, 3.8 Hz, 1H), 2.55 (s, 1H), 2.30 (d, J=11.8, 6.4 Hz, 1H), 2.23 (I, J=7.2 Hz, 2H), 1.90 (dd, J=12.4, 6.6 Hz, 1H), 1.86-1.74 (m, 1H), 1.61 (d, J=14.4 Hz, 3H), 1.59-1.48 (m, 3H), 1.48-1.40 (m, 3H), 1.36 (s, 3H), 1.10 (d, J=7.0 Hz, 3H), 0.81 (d, J=5.8 Hz, 3H), 0.73 (d, J=5.8 Hz, 3H).

Product 44

$^1$H NMR (400 MHZ, CDCl$_3$) δ 8.60 (d, J=4.4 Hz, 1H), 8.50 (d, J=8.8 Hz, 1H), 8.03 (d, J=7.6 Hz, 1H), 7.83 (dd, J=8.4, 7.2 Hz, 1H), 7.44 (dd, J=6.8, 5.2 Hz, 1H), 7.17 (dd, J=16.0, 7.2 Hz, 2H), 7.05 (s, 2H), 6.91 (d, J=7.8 Hz, 1H), 6.59 (d, J=8.8 Hz, 1H), 5.07-5.00 (m, 1H), 3.89 (s, 3H), 3.87-3.81 (m, 2H), 3.80-3.71 (m, 1H), 3.60-3.46 (m, 2H), 3.37 (dd, J=14.3, 4.3 Hz, 1H), 3.19 (t, J=13.6 Hz, 1H), 3.13-3.01 (m, 2H), 2.81-2.71 (m, 1H), 2.67 (dd, J=20.0, 8.7 Hz, 2H), 2.30 (d, J=13.1 Hz, 1H), 2.08 (s, 1H), 2.02-1.92 (m, 1H), 1.87-1.79 (m, 2H), 1.12 (d, J=6.8 Hz, 3H).

The above are only the preferred embodiments of the present invention. It should be noted that improvements and modifications can be made by those of ordinary skill in the art without departing from the principle of the present invention, which should also be regarded as falling within the protection scope of the present invention.

The invention claimed is:

1. A precursor of cyclic peptide compound simulating natural product structure, having general structural formula I:

Formula I

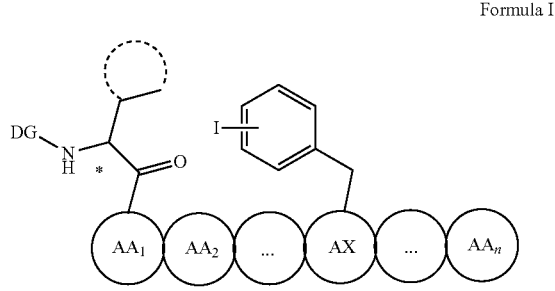

wherein DG is a directing group which is any one selected from the following groups:

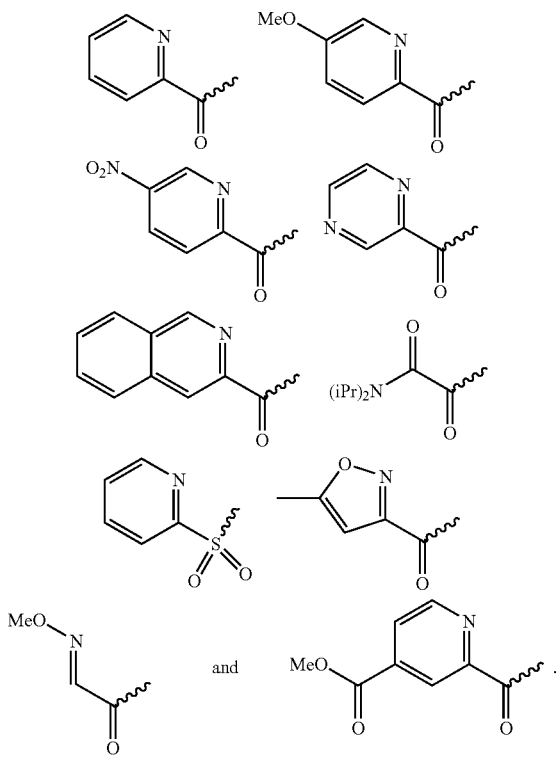

AA$_1$ to AA$_n$ represent a peptide chain, n represents length of the peptide chain, and the value range of n is 3-10; wherein a peptide chain segment corresponding to AA$_3$ to AA$_n$ comprises at least one aryl iodide side chain, and the part comprising the aryl iodide side chain in the peptide chain segment is denoted as

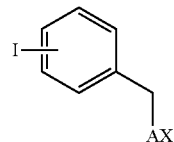

* represents a chiral center and

represents an alkyl side chain.

2. The precursor of cyclic peptide compound simulating natural product structure according to claim 1, wherein

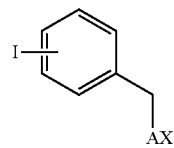

in the peptide chain is one selected from the group consisting of 3-iodophenylalanine, 3-iodotyrosine, 3-iodo-p-methoxyphenylalanine, 4-iodophenylalanine and a compound formed by assembling aryl iodobenzene on the side chain of lysine, serine, or glutamic acid.

3. The precursor of cyclic peptide compound simulating natural product structure according to claim 1, wherein AX is located at the terminal position AA$_n$ end of the peptide chain segment corresponding to AA$_3$ to AA$_n$.

4. The precursor of cyclic peptide compound simulating natural product structure according to claim 3, wherein

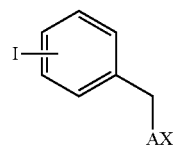

is 3-iodobenzylamine or 3-iodophenethylamine.

5. The precursor of cyclic peptide compound simulating natural product structure according to claim 1, wherein the amino acids other than AX in the peptide chain are selected from the group consisting of α-amino acids, 3-aminopropionic acid, 4-aminobutyric acid, 5-aminovaleric acid, 6-aminobutyric acid, 7-aminoheptanoic acid and 8-aminooctanoic acid.

6. The precursor of cyclic peptide compound simulating natural product structure according to claim 5, wherein the α-amino acid is selected from the group consisting of glycine, alanine, proline, N-Me-alanine, 2-aminobutyric acid, 2-aminopentanoic acid, valine, isoleucine, leucine, tert-leucine, phenylalanine, threonine, serine, lysine, arginine, glutamic acid, glutamine, aspartame acid, asparagine, tryptophan, cysteine, methionine, tyrosine, histidine and cyclohexylglycine.

7. The precursor of cyclic peptide compound simulating natural product structure according to claim 1, wherein the alkyl side chain is selected from the group consisting of ethyl, propyl, isopropyl, isobutyl, cyclopropyl, cyclobutyl, cyclopentyl, cyclohexyl, allyl and phenyl.

8. A preparation method for cyclic peptide compound from the precursor of cyclic peptide compound simulating natural product structure according to claim 1, comprising the following steps: subjecting a compound of formula I, a divalent palladium catalyst, and a silver salt to intramolecular arylation reaction under heating and stirring in a solvent to construct a cyclic peptide to produce a compound having general structural formula II:

Formula II

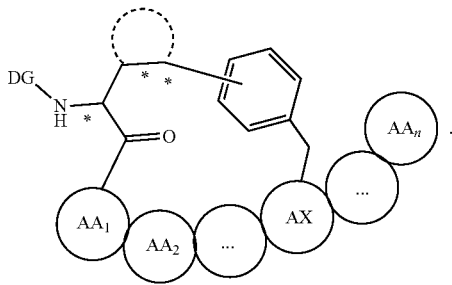

9. The preparation method for cyclic peptide compound simulating natural product structure according to claim 8, wherein the concentration of the compound of formula I in the solvent is 50-200 mM, and the molar ratio of the compound of formula I:the divalent palladium catalyst: the silver salt is 1:0.05-0.15:1.5-3.0.

10. The preparation method for cyclic peptide compound simulating natural product structure according to claim 8, wherein the solvent is any one selected from the group consisting of hexafluoroisopropanol, chlorobenzene, trifluoroethanol, dichloroethane, tert-amyl alcohol, water, and a mixed solvent of hexafluoroisopropanol and water at a volume ratio of 1:0-1:2.

11. The preparation method for cyclic peptide compound simulating natural product structure according to claim 8, wherein the divalent palladium catalyst is one selected from the group consisting of $Pd(CH_3CN)_4(BF_4)_2$, $Pd(OAc)_2$, $Pd(TFA)_2$, $Pd(OPiv)_2$ and $Pd(CH_3CN)_2Cl_2$; and the silver salt is one selected from the group consisting of silver acetate, silver benzoate, silver carbonate, silver oxide and silver phosphate.

12. The preparation method for cyclic peptide compound simulating natural product structure according to claim 8, wherein reaction condition of the intramolecular arylation reaction includes a heating temperature of 110-130° C. and a reaction time of 6-48 hours.

13. The precursor of cyclic peptide compound simulating natural product structure according to claim 3, wherein

in the peptide chain is one selected from the group consisting of 3-iodophenylalanine, 3-iodotyrosine, 3-iodo-p-methoxyphenylalanine, 4-iodophenylalanine and a compound formed by assembling aryl iodobenzene on the side chain of lysine, serine, or glutamic acid.

* * * * *